US010278786B2

(12) United States Patent
Friedrich et al.

(10) Patent No.: US 10,278,786 B2
(45) Date of Patent: May 7, 2019

(54) RETRACTING TISSUE

(71) Applicant: GLOBUS MEDICAL, INC, Audubon, PA (US)

(72) Inventors: Adam Friedrich, Cinnaminson, NJ (US); Mark Weiman, Coatesville, PA (US); Matthew Bechtel, Norristown, PA (US); Varun Ponmudi, Philadelphia, PA (US); Daniel Wolfe, Hatfield, PA (US); Hilliary Adams, Conshohocken, PA (US); John Matthews, Philadelphia, PA (US)

(73) Assignee: Globus Medical, Inc., Audubon, PA (US)

(*) Notice: Subject to any disclaimer, the term of this patent is extended or adjusted under 35 U.S.C. 154(b) by 0 days.

(21) Appl. No.: 15/019,001

(22) Filed: Feb. 9, 2016

(65) Prior Publication Data
US 2016/0192922 A1    Jul. 7, 2016

Related U.S. Application Data

(63) Continuation-in-part of application No. 14/664,089, filed on Mar. 20, 2015, now Pat. No. 10,039,539, which is a continuation-in-part of application No. 14/183,048, filed on Feb. 18, 2014.

(51) Int. Cl.
A61B 1/32        (2006.01)
A61B 90/30       (2016.01)
A61B 17/02       (2006.01)

(52) U.S. Cl.
CPC .......... *A61B 90/30* (2016.02); *A61B 17/0206* (2013.01); *A61B 1/32* (2013.01); *A61B 17/0293* (2013.01)

(58) Field of Classification Search
CPC ............ A61B 17/0206; A61B 17/0293; A61B 17/025; A61B 1/32; A61B 1/0676; A61B 2017/00473
USPC ......... 600/201, 210–219, 226–234, 241, 245
See application file for complete search history.

(56) References Cited

U.S. PATENT DOCUMENTS

| 4,616,635 A | * | 10/1986 | Caspar | A61B 17/02 600/215 |
| 5,363,841 A | * | 11/1994 | Coker | A61B 17/0206 600/211 |
| 5,928,139 A | * | 7/1999 | Koros | A61B 17/0206 600/205 |
| 5,944,658 A | * | 8/1999 | Koros | A61B 17/0206 600/231 |
| 6,083,154 A | * | 7/2000 | Liu | A61B 17/0293 600/231 |
| 6,139,493 A | | 10/2000 | Koros | |

(Continued)

FOREIGN PATENT DOCUMENTS

JP    2012-507368 A    3/2012
JP    2013-509982 A    3/2013
(Continued)

*Primary Examiner* — Zade Coley
*Assistant Examiner* — Jessica Weiss

(57) ABSTRACT

Surgical retractors and methods thereof for retracting body tissue in a therapeutic procedure. The surgical retractor may include retractor blades have openings or channels configured to receive bone pins while maintaining accessibility and visibility of the operative window.

16 Claims, 36 Drawing Sheets

(56) References Cited

U.S. PATENT DOCUMENTS

| | | | |
|---|---|---|---|
| 6,206,826 B1* | 3/2001 | Mathews | A61B 17/025 600/210 |
| 8,062,218 B2 | 11/2011 | Sebastian et al. | |
| 8,353,826 B2* | 1/2013 | Weiman | A61B 17/0206 600/219 |
| 2004/0193018 A1 | 9/2004 | Thalgott et al. | |
| 2006/0224044 A1 | 10/2006 | Marchek et al. | |
| 2006/0247645 A1* | 11/2006 | Wilcox | A61B 17/025 606/86 R |
| 2007/0073111 A1 | 3/2007 | Bass | |
| 2008/0188718 A1 | 8/2008 | Spitler et al. | |
| 2009/0203969 A1 | 8/2009 | Cohen et al. | |
| 2009/0227845 A1 | 9/2009 | Lo et al. | |
| 2010/0113885 A1 | 5/2010 | McBride et al. | |
| 2011/0224496 A1 | 9/2011 | Weiman | |
| 2011/0301423 A1 | 12/2011 | Koros et al. | |
| 2012/0245432 A1 | 9/2012 | Karpowicz et al. | |
| 2012/0303034 A1* | 11/2012 | Woolley | A61B 17/0206 606/90 |
| 2012/0316400 A1 | 12/2012 | Vijayanagar | |
| 2013/0096387 A1 | 4/2013 | Deridder et al. | |
| 2014/0330086 A1* | 11/2014 | Mire | A61B 17/0218 600/215 |

FOREIGN PATENT DOCUMENTS

| | | |
|---|---|---|
| JP | 2013-537467 A | 10/2013 |
| WO | 02078525 A2 | 10/2002 |
| WO | 2006116336 A2 | 11/2006 |
| WO | 2012026981 A1 | 3/2012 |

* cited by examiner

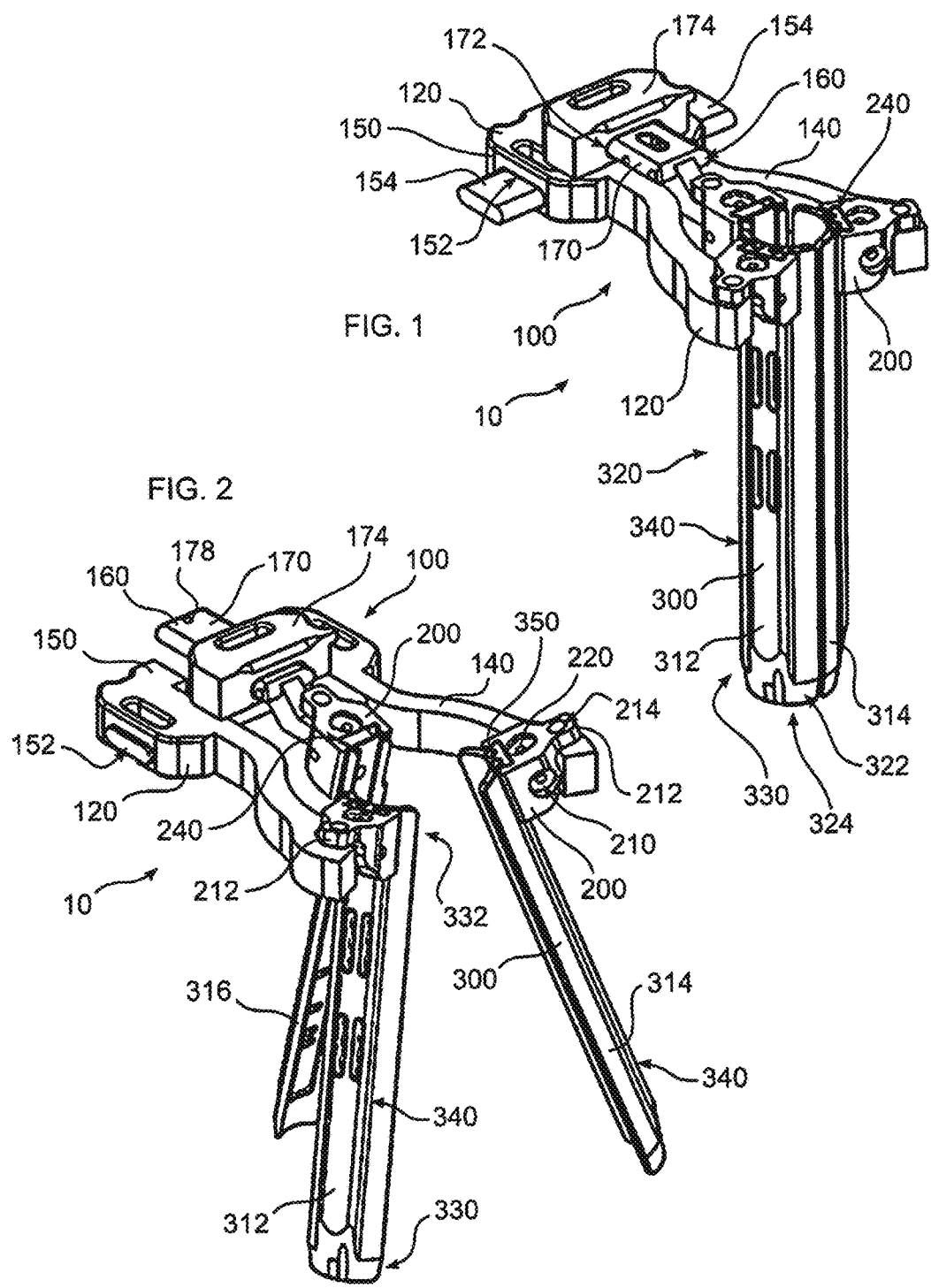

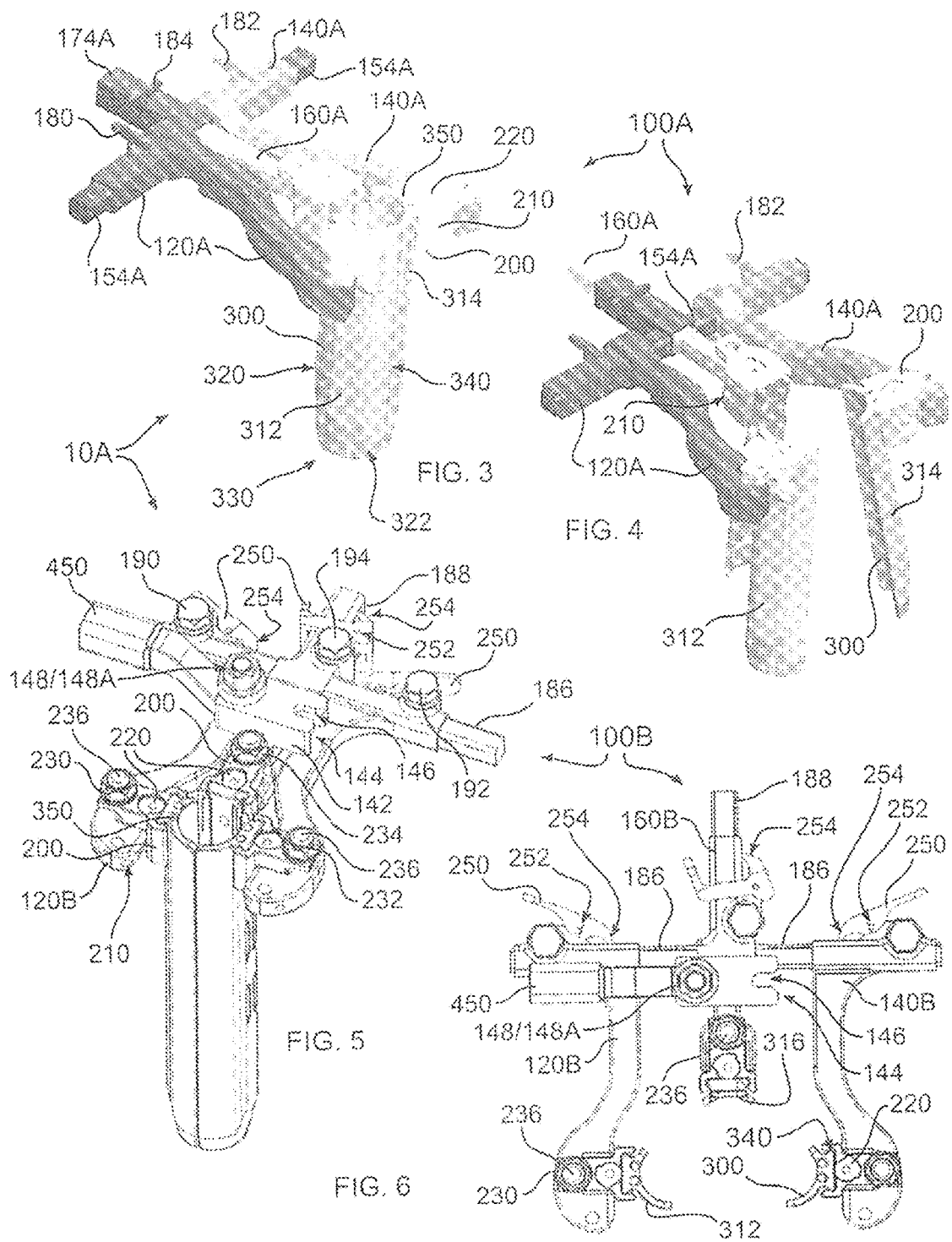

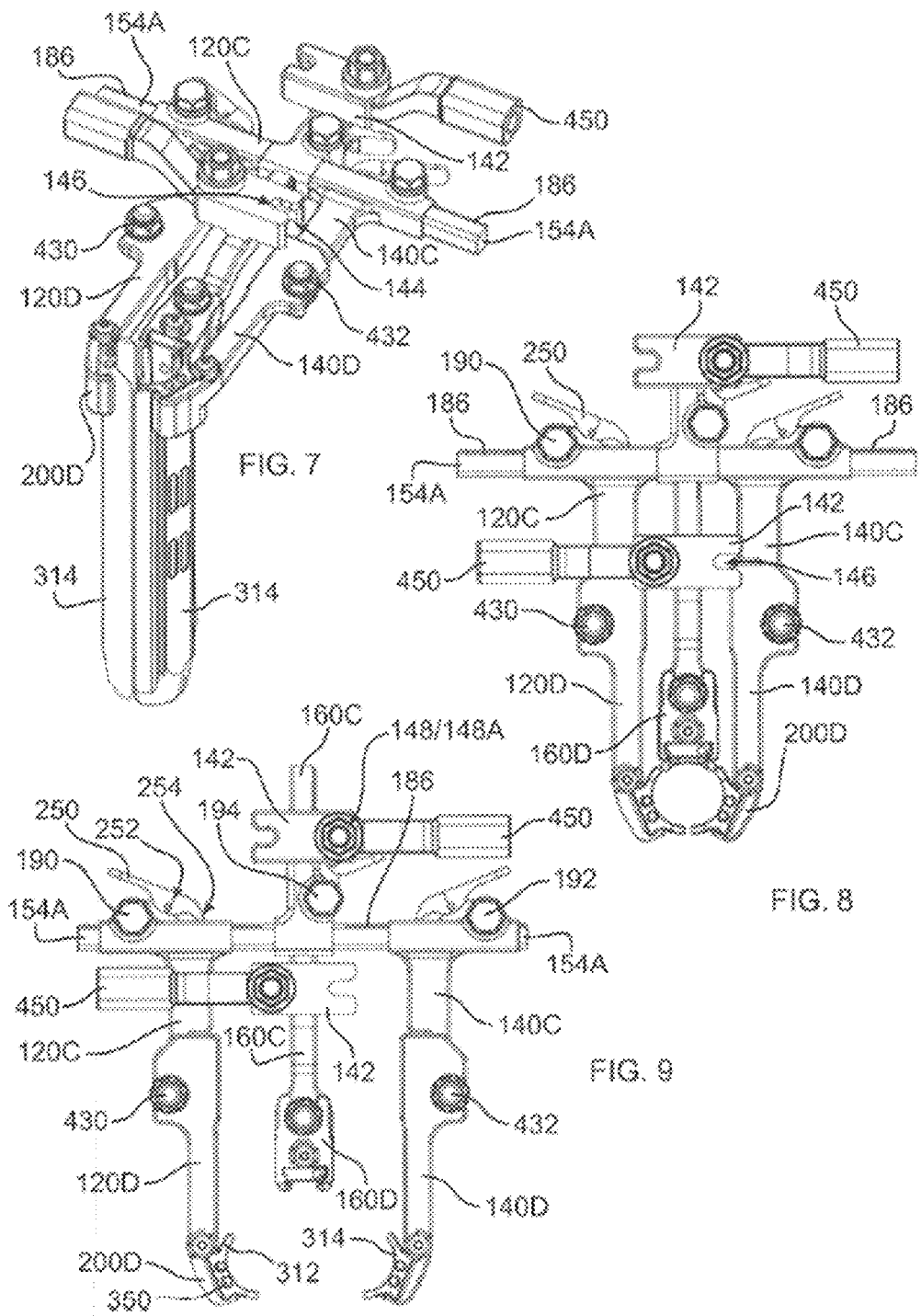

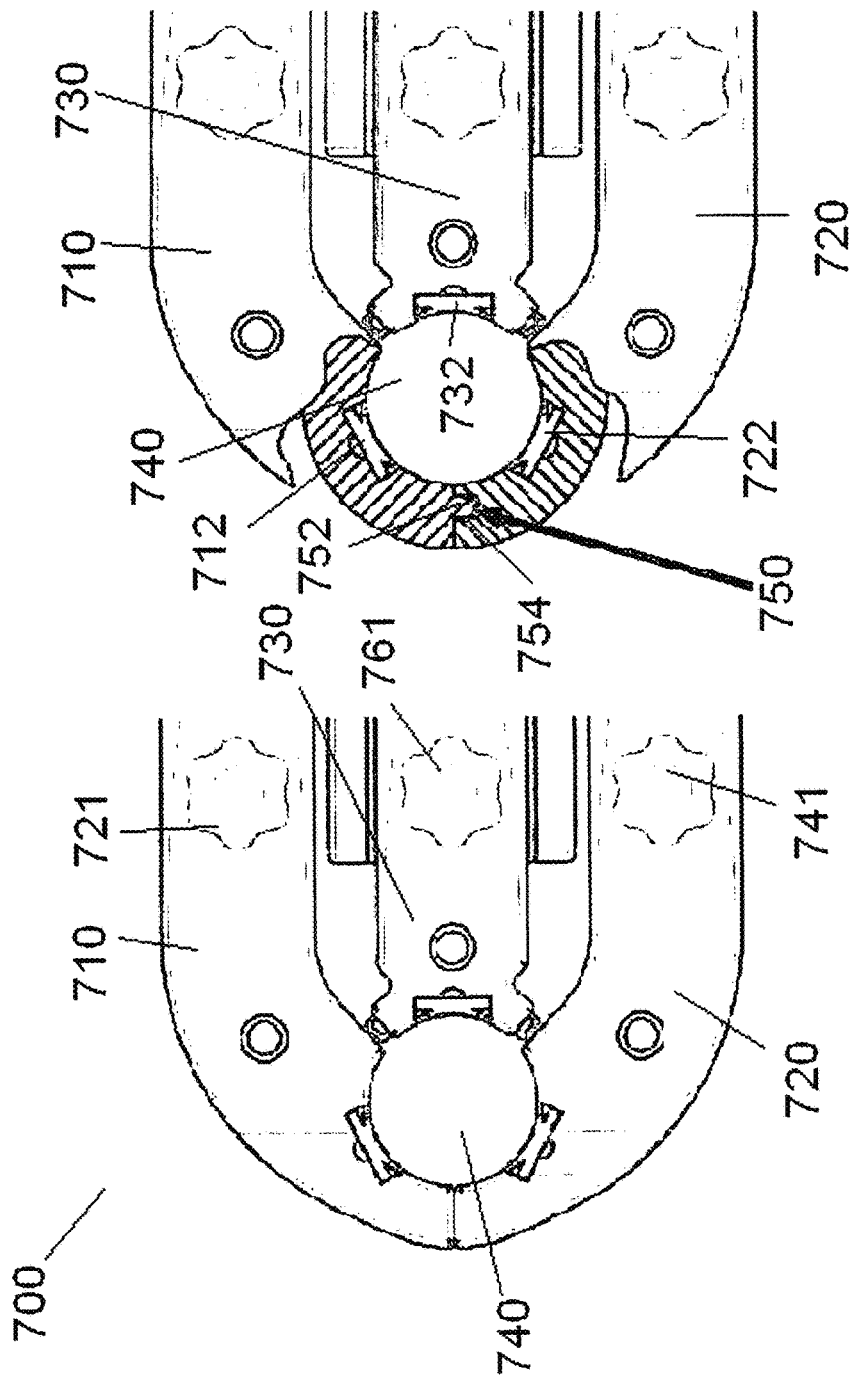

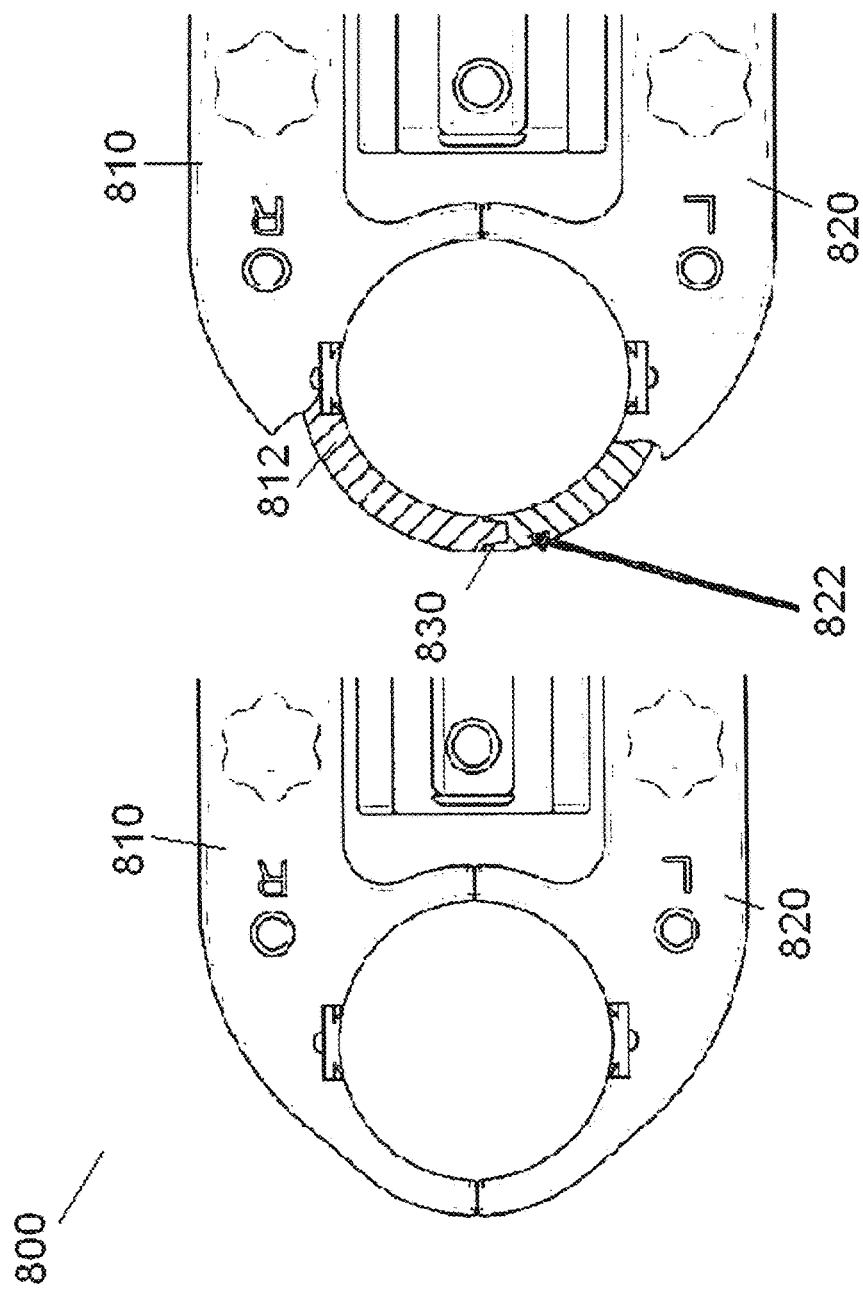

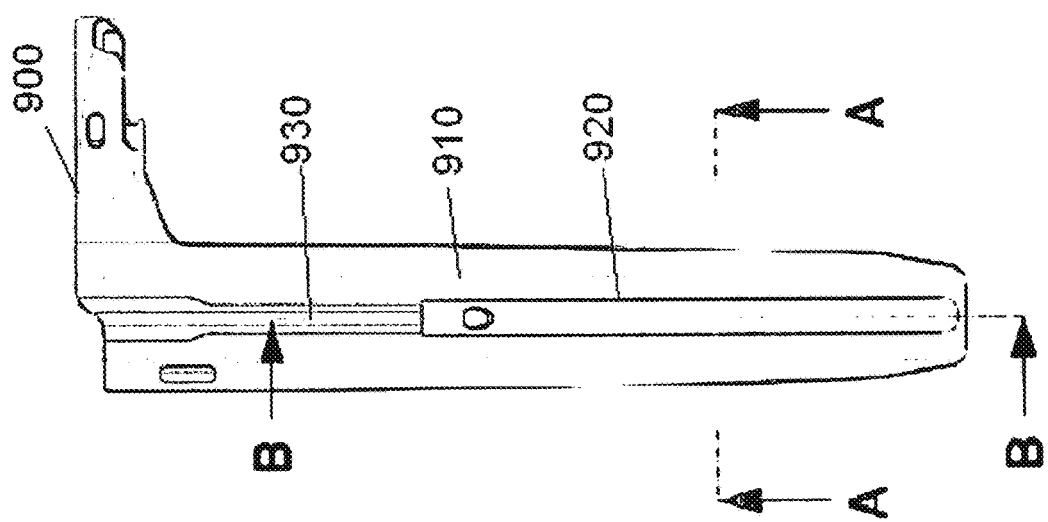

B-B

A-A

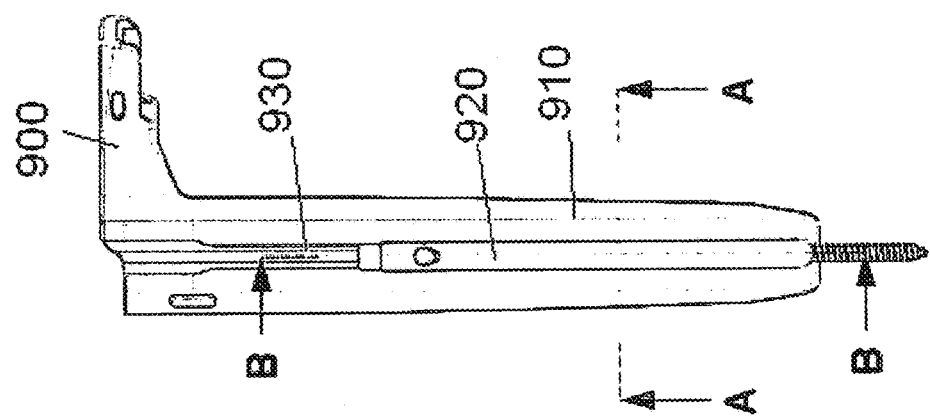

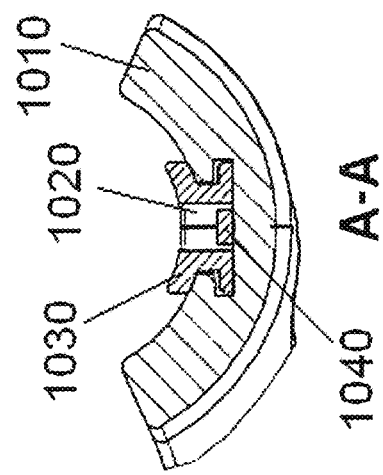
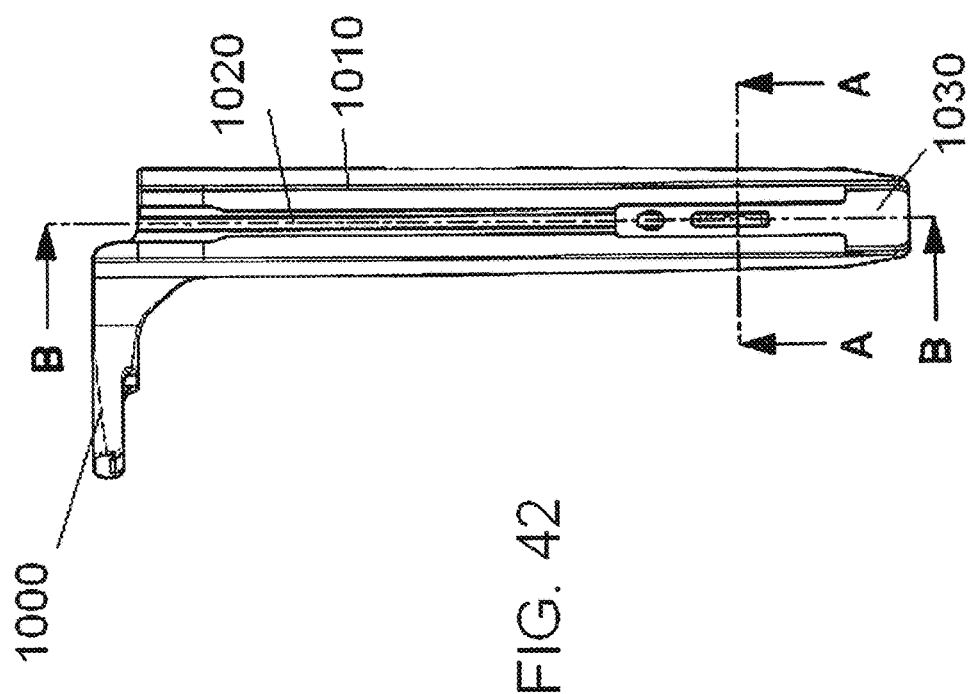

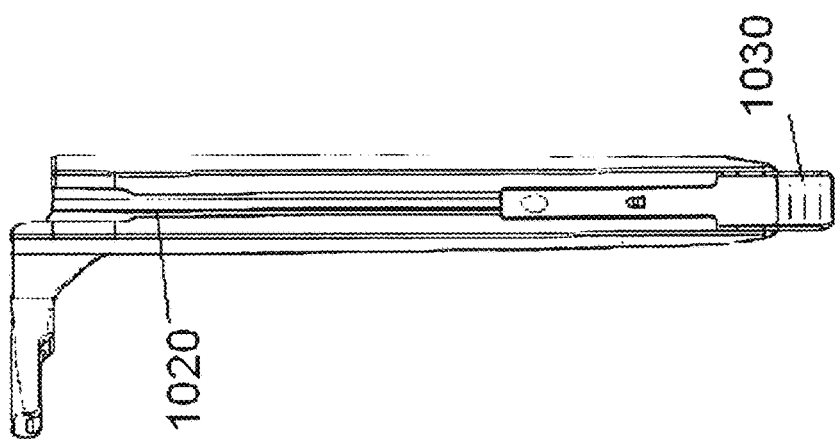
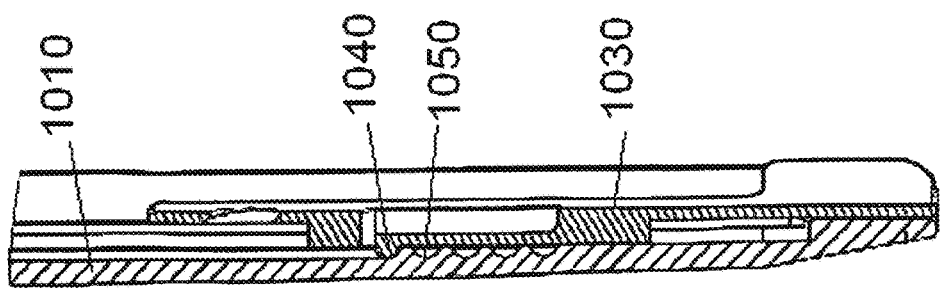

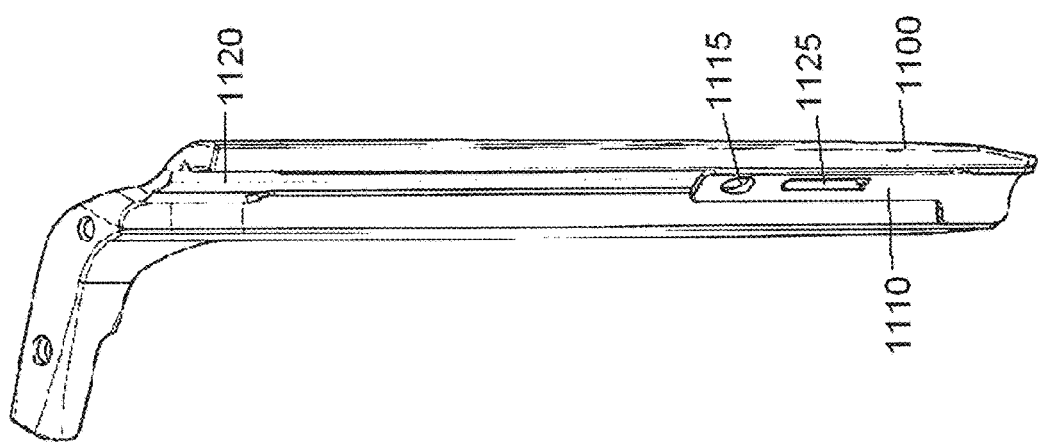

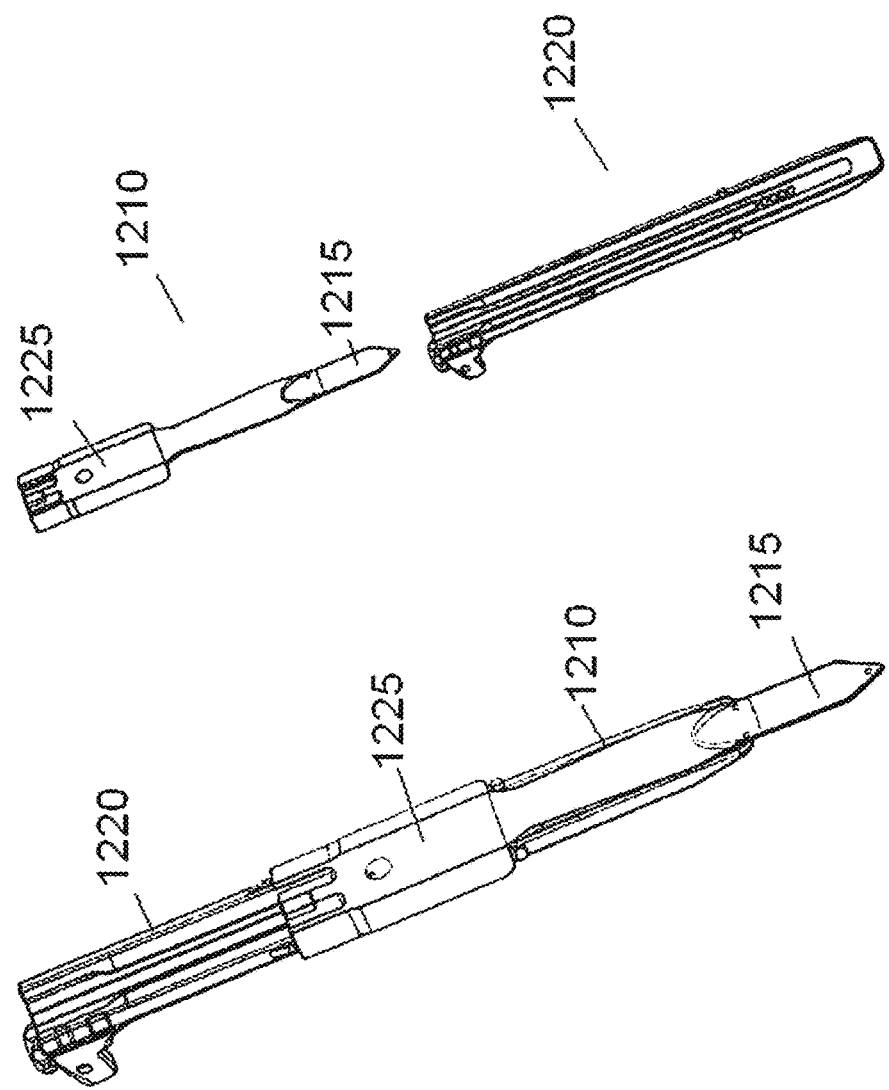

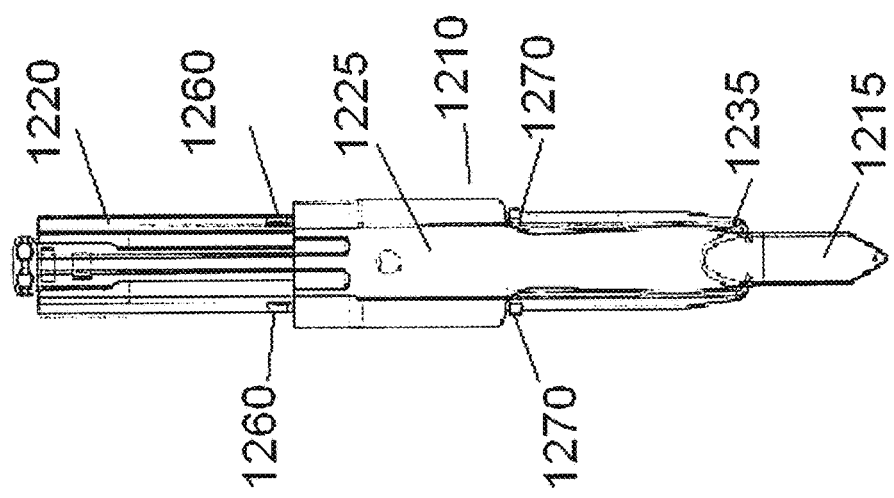

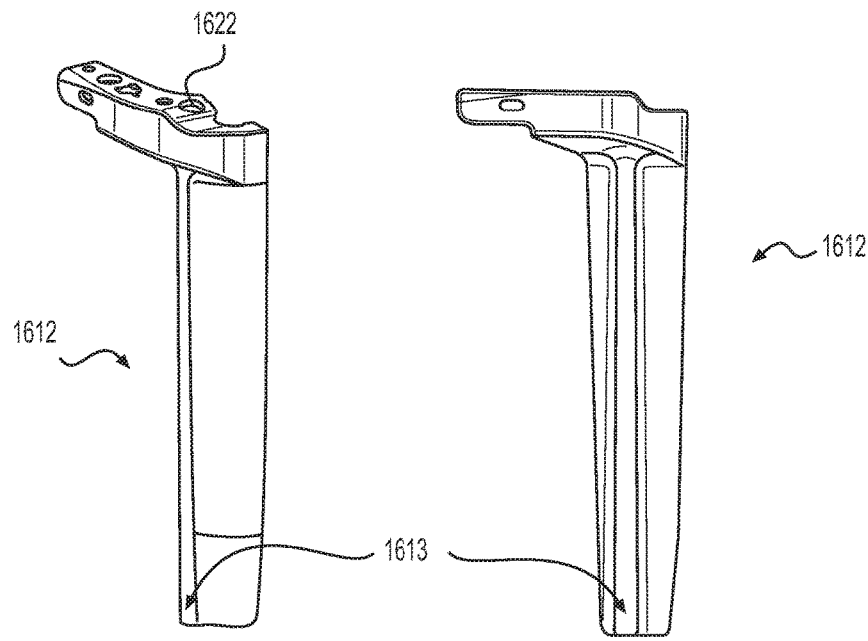
FIG. 53A  FIG. 53B
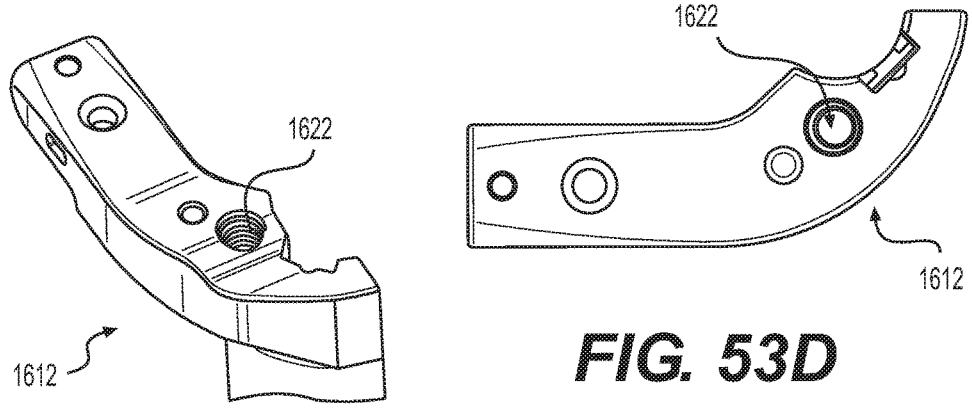
FIG. 53C  FIG. 53D

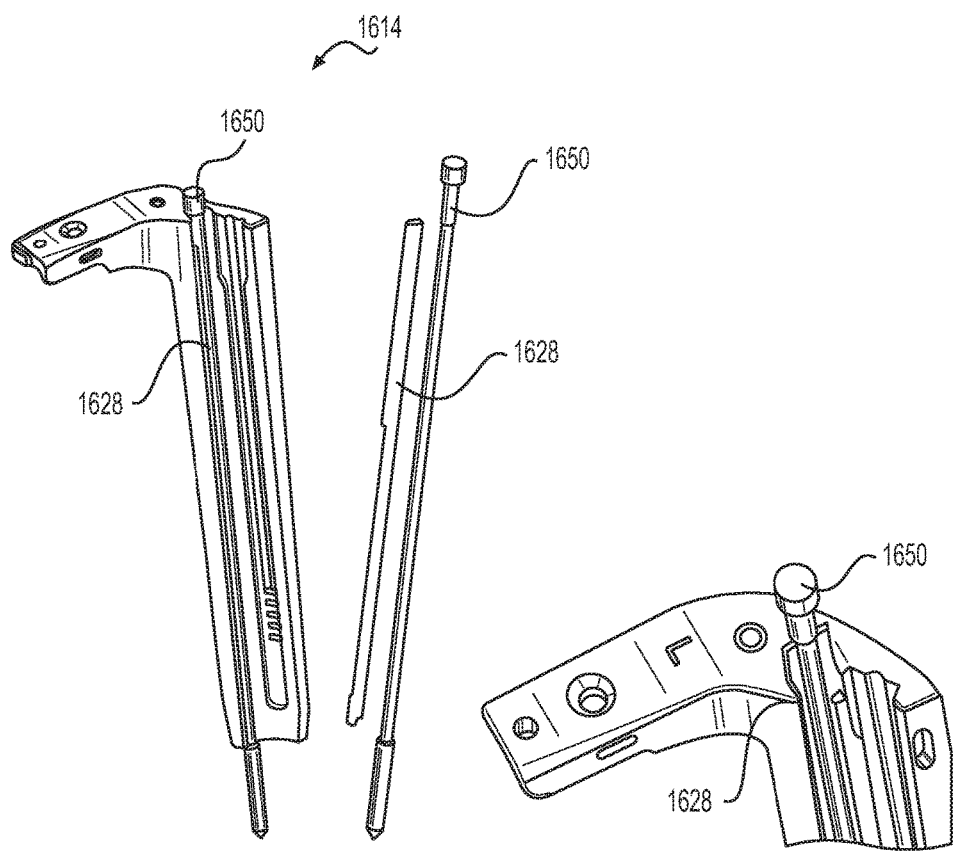
*FIG. 57A*  *FIG. 57B*

RETRACTING TISSUE

CROSS-REFERENCE TO RELATED APPLICATIONS

The present application is a continuation-in-part of U.S. application Ser. No. 14/664,089, filed Mar. 20, 2015, which is a continuation-in-part application of Ser. No. 14/183,048, filed Feb. 18, 2014, which are hereby incorporated by reference in their entireties for all purposes.

FIELD OF THE INVENTION

The invention relates to a system and method for retracting body tissue during surgery, and more particularly to multi-axis retractors affixed to a base.

BACKGROUND OF THE INVENTION

Retractor systems may be used in a variety of different surgical procedures to provide an opening through which a doctor may access the surgical site. In spinal surgeries, for example, a retractor system may be used to provide the surgeon with access to the patient's spine. The opening created by the retractor system may, for example, enable the doctor to insert surgical instruments into the body or enable visualization of the surgical site using visible light or X-rays.

A retractor system may include a plurality of blades coupled to a retractor frame. In use, the blades may be inserted into an incision and then retracted to displace tissue surrounding the incision along a path to the surgical site. To minimize trauma to the tissue, this tissue displacement should generally be refined and controlled.

SUMMARY OF THE INVENTION

In accordance with an embodiment of the disclosure, a surgical retractor for retracting body tissue in a therapeutic procedure comprises at least one first arm defining proximal and distal ends and a first arm longitudinal axis extending therebetween, the distal end configured to support a retractor blade, the proximal end forming one of an extension or a block having an aperture; at least one second arm defining proximal and distal ends and a second arm longitudinal axis extending therebetween, the distal end configured to support a retractor blade, the proximal end forming one of an extension or a block having an aperture; a core: (a) configured to form a slideable connection each with the at least one first arm and the at least one second arm, (b) the slideable connection with the at least one first arm formed as a block having an aperture when the proximal end of the at least one first arm forms an extension, the slideable connection formed as an extension when the proximal end of the at least one first arm forms a block having an aperture, (c) the slideable connection with the at least one second arm formed as a block having an aperture when the proximal end of the at least one second arm forms an extension, the slideable connection formed as an extension when the proximal end of the at least one second arm forms a block having an aperture, (d) each first arm translatable using the slideable connection independently of translation of at least one second arm, (e) each second arm translatable using the slideable connection independently of translation of at least one first arm, and (f) the distal end of at least one first arm and the distal end of at least one second arm mutually separateable using the slideable connection to thereby separate retractor blades supported upon the at least one first arm and the at least one second arm.

In variations thereof, each first arm is translatable using the slideable connection along an axis transverse to the first longitudinal axis, and each second arm is translatable using the slideable connection along the second longitudinal axis; there are two first arms and one second arm; the two first arms and one second arm formable into a cannula; one or more retractor blades have a tapered end configured to retract tissue that is bone; at least one retractor blade is pivotally mounted to at least one of the at least one first arm and the at least one second arm; pivoting the at least one retractor blade retracts tissue, and separating at least one first arm from at least one second arm retracts tissue; and/or at least one retractor blade is pivoted by rotating a threaded shaft.

In further variations thereof, the retractor further includes at least one blade holder pivotally mounted to at least one of the at least one first arm and the at least one second arm; a blade is connected to each of the at least one blade holder using a dovetail connection; and/or a light source is affixable to at least one retractor blade.

In yet further embodiments thereof, the therapeutic procedure is conducted in a surgical facility having a supporting surface including an extension arm, the retractor further including a mount moveably connected to the core and configured to releasably connect to the extension arm; and/or the mount is moveably connected to the core by a pivot.

In other variations thereof, the slideable connection between at least one of the first and second arms and the core includes a rack and a mating ratcheting pawl, the rack and pawl configured to control relative movement of the at least one first and second arm and the core; the retractor further includes a pinion rotatably secured to one of the at least one first and second arms and the core, the rack associated with the other of the at least one first and second arm, the pinion rotatable to change a relative position of the at least one first and second arm and the core; and/or the retractor further includes at least one of a manually engageable key and a tool engagement connected to the pinion, the key or the tool engagement rotatable to rotate the pinion.

In other embodiments thereof, the retractor further includes a blade holder including a block affixed to at least one of the at least one first and second arms and defining an aperture and an extending flange; a blade retainer having an extension sized and dimensioned to be insertable into the aperture; a threadable set screw connectable between the blade retainer and the extending flange to retain the blade retainer in connection with the block; and/or the retractor further includes a blade holder including a block affixed to at least one of the at least one first and second arms and defining an aperture and an extending flange; a retractor blade having an extension sized and dimensioned to be insertable into the aperture; a threadable set screw connectable between the retractor blade and the extending flange to retain the retractor blade in connection with the block.

In another embodiment of the disclosure, a surgical retractor for retracting body tissue in a therapeutic procedure comprises at least one first arm defining proximal and distal ends and a first arm longitudinal axis extending therebetween, the proximal end defining a first block having a first aperture, the first aperture defining a first aperture longitudinal axis that is transverse to the first arm longitudinal axis, the distal end configured to support a retractor blade; a transverse extension extending through and slideably supporting at least one first block of the at least one first arm; at least one second arm defining proximal and distal ends and a second arm longitudinal axis extending therebetween, the proximal end defining a second extension, the distal end configured to support a retractor blade; and a second block connected to the transverse extension and having a second aperture sized and dimensioned to slideably support at least one second extension, the second aperture defining a second aperture longitudinal axis that is non-parallel with respect to the first aperture longitudinal axis, each second arm translatable in connection with the second block along the second longitudinal axis, each first arm translatable in connection with the transverse extension along the first aperture longitudinal axis, at least one first arm translatable independently of translation of at least one second arm, and at least one second arm translatable independently of translation of at least one first arm.

In a yet further embodiment of the disclosure, a surgical retractor for retracting body tissue in a therapeutic procedure comprises at least one first arm defining proximal and distal ends and a first arm longitudinal axis extending therebetween, the distal end configured to support a retractor blade, the proximal end forming one of an extension or a block having an aperture; at least one second arm defining proximal and distal ends and a second arm longitudinal axis extending therebetween, the distal end configured to support a retractor blade, the proximal end forming one of an extension or a block having an aperture; a core: (a) configured to form a slideable connection each with the at least one first arm and the at least one second arm, (b) the slideable connection with the at least one first arm formed as a block having an aperture when the proximal end of the at least one first arm forms an extension, the slideable connection formed as an extension when the proximal end of the at least one first arm forms a block having an aperture, (c) the slideable connection with the at least one second arm formed as a block having an aperture when the proximal end of the at least one second arm forms an extension, the slideable connection formed as an extension when the proximal end of the at least one second arm forms a block having an aperture, (d) each first arm translatable using the slideable connection along an axis transverse to the first longitudinal axis, at least one first arm translatable independently of translation of at least one second arm, (e) each second arm translatable using the slideable connection along the second longitudinal axis, at least one second arm translatable independently of translation of at least one first arm, and (f) the distal end of at least one first arm and the distal end of at least one second arm mutually separateable using the slideable connection to thereby separate retractor blades supported upon the at least one first arm and the at least one second arm.

In accordance with some exemplary embodiments, a retractor system can be provided, comprising a first arm having a first retractor blade configured to displace tissue, a second arm having a second retractor blade configured to displace tissue, and an engagement mechanism for engaging the first blade with the second blade to prevent movement between the first and second blades when the retractor system is in a non-extended position.

The retractor system can further comprise a third arm configured to support a posterior blade configured to displace tissue. The first arm, second arm and third arm can each be configured to be linearly translatable to be moveable with respect to each other. The engagement mechanism can be configured to lock the first blade with the second blade to prevent movement between the first and second blades. The engagement mechanism can comprise a tab disposed along a length of the first blade, and a slot configured along a corresponding length of the second blade configured to receive the tab.

The retractor system can further comprise a first docking pin sleeve provided in the first blade configured to receive a docking pin, and a first docking pin configured for placement in the first docking pin sleeve and configured to be threaded into a vertebral body of a patient to secure the retractor system.

The retractor system can further comprise a lengthening shim provided in the first blade configured to extend past a lower tip of the first blade to prevent tissue creep into the first blade. The retractor system can further comprise one or more detent stops provided along fixed, incremental locations along a length of the first blade. The retractor system can further comprise a lengthening shim detent tab configured to engage with one or more detent stops to allow for an adjustable height of the lengthening shim along the fixed, incremental locations. The one or more detent stops can be provided in 2.5 millimeter intervals. The retractor system can further comprise a lengthening shim removal hole on the lengthening shim configured to disengage the lengthening shim detent tab from the one or more detent stops using a removal tool.

The retractor system can further comprise a widening shim provided along a lower portion of the first blade configured to extend past a lower tip of the first blade in a direction towards the second blade to prevent tissue creep. The retractor system can further comprise one or more detent stops provided along fixed, incremental locations along a width of the first blade. The retractor system can further comprise a widening shim detent tab configured to engage with the one or more detent stops to allow the widening shim to extend past the first blade along the fixed, incremental locations. The one or more detent stops can be provided in 1 millimeter intervals. The retractor system can further comprise a widening shim removal hole on the widening shim configured to disengage the widening shim detent tab from the one or more detent stops using a removal tool. The retractor system can further comprise one or more etched areas along a blade tip of the first blade for neuromonitoring.

The retractor system can further comprise a third arm having a posterior blade configured to displace tissue, and a disc shim secured to the posterior blade extending below the third blade to anchor the posterior blade into a disc space.

In some exemplary embodiments, a retractor system can be provided, comprising a first arm located around a central bore of the retractor system supporting a first retractor blade configured to displace tissue and configured to be translated independently, a second arm located around the central bore in proximity to the first arm and supporting a second retractor blade configured to displace tissue and configured to be translated independently, a tab disposed on a fixed location along a length of the first blade, and a slot disposed on a fixed location along a length of the second blade corresponding to the tab and configured to receive the tab to engage the first blade with the second blade and prevent movement of the first blade with respect to the second blade when the retractor system is in a non-retracted position.

In other exemplary embodiments, one or more of the retractor blades includes an opening extending from a first end to a second end of the blade. The opening is configured to receive a bone pin, which engages adjacent bone. The opening may be a partial channel in fluid communication with an interior of the blade. The channel may have a semi-circular cross-section and may extend along an entire length of the blade. In some embodiments, a portion of the channel may be threaded. In other embodiments, an insert, configured to receive a portion of the bone pin, may be positioned within the partial channel. The sleeve and/or pin may be at least partially contained within the blade, thereby moving the bone pin closer to the working channel for improved visibility while still keeping the bone pin out of the working window.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 depicts a surgical retractor blade holder of the disclosure, the blades held in a configuration conforming to a cannula;

FIG. 2 depicts the retractor of FIG. 1, the blades relatively separated in a manner operative to retract tissue of the body in a therapeutic procedure;

FIG. 3 depicts a retractor of the disclosure, including manually operable adjustment mechanisms for separating blades of the retractor, the blades in a closed configuration;

FIG. 4 depicts the retractor of FIG. 3, the blades in an opened configuration;

FIG. 5 depicts an alternative retractor of the disclosure, including adjustment mechanisms operable with a tool, the blades in a closed configuration;

FIG. 6 depicts the retractor of FIG. 5, the blades in an opened configuration;

FIG. 7 depicts an alternative retractor of the disclosure, including articulated blade holding arms, and a plurality of frame mounts of the disclosure;

FIG. 8 depicts a top view of the retractor of FIG. 7;

FIG. 9 depicts a top view of the retractor of FIG. 7, the blades in an opened position;

FIG. 32 depicts a top view of a portion of a three-blade retractor system in a closed or non-retracted position in accordance with some embodiments;

FIG. 33 depicts a top view of the retractor system of FIG. 32, with a portion removed to show mateable blade features in accordance with some embodiments;

FIG. 35 depicts a top view of a portion of a two-blade retractor system in a closed or non-retracted position in accordance with some embodiments;

FIG. 36 depicts a top view of the retractor system of FIG. 35, with a portion removed to show mateable blade features in accordance with some embodiments;

FIG. 38 depicts a blade having a docking pin sleeve in accordance with some embodiments;

FIG. 41 depicts a docking pin inside a docking pin sleeve in accordance with some embodiments;

FIG. 42 depicts a blade having a lengthening shim in accordance with some embodiments;

FIG. 43 depicts a cross-sectional view taken along line A-A of FIG. 42;

FIG. 44 depicts a cross-sectional view taken along line B-B of FIG. 42;

FIG. 45 depicts a blade having a widening shim in accordance with some embodiments;

FIG. 46 depicts a top perspective view of the blade having the widening shim of FIG. 45;

FIG. 49 depicts a perspective view of a portion of a blade including a disc shim in accordance with some embodiments;

FIG. 50 depicts a view of a blade separated from a disc shim in accordance with some embodiments;

FIG. 51 depicts a front view of a blade having a disc shim in accordance with some embodiments;

FIGS. 53A-53D shows several alternative views of a retractor blade according to one embodiment;

FIGS. 57A-57B depict an alternative embodiment of a retractor blade with an insert for the bone pin according to yet another embodiment.

DETAILED DESCRIPTION OF THE INVENTION

Figure 10:
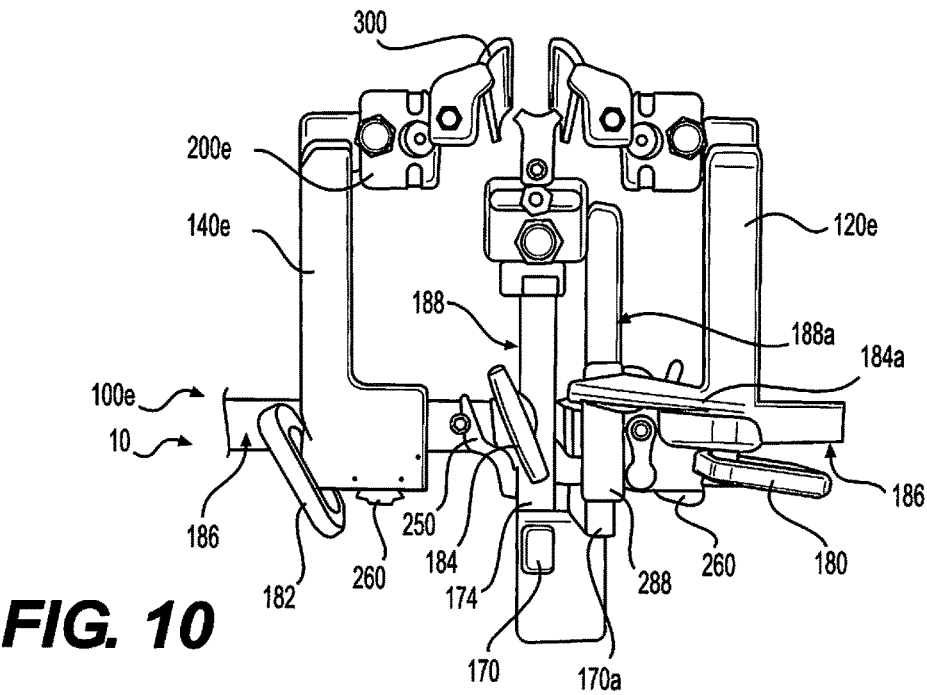
FIG. 10 depicts an alternative embodiment of a retractor of the disclosure, illustrating a thumbwheel operated rack and pinion adjustment mechanism.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

FIGS. 1-2 illustrate a retractor system 10 that can be used to retract a patient's body tissue in a surgical procedure in accordance with one embodiment of the present disclosure. Retractor system 10 includes a plurality of retractor blades 300, and in this embodiment, a first blade 312, a second blade 314, and a third blade 316. Blades 300 are each coupled to a retractor frame 100, which includes first, second, and third arms 120, 140, and 160, each having a blade holder 200 for holding and positioning a blade 300. In one use of this embodiment, arms 120 and 140 are cranial/caudal blades, and blade 160 is a posterior blade, although other orientations and uses are contemplated. In an embodiment, each blade may be translated or indexed freely without a requirement to index another blade. In the embodiment shown, arms 120 and 140 are laterally located, and arm 160 is centrally located, although other relative dispositions are contemplated within the disclosure.

Retractor 10 is configured to be adjusted into a desired position, and then releasably fixed to an operating table or other object in the operating theatre, so that a relative position of retractor 10 and a patient can be controlled. Fixation of one or more of retractor 10 can be accomplished using one or more of an operating room (OR) table clamp, a retractor table arm, an arm clamp, and a frame clamp, for example.

Arms 120, 140, and 160 are each linearly translatable to be moveable with respect to each other. More particularly, arms 120 and 140 each include a base 150 having a slot 152, sized to mateably receive and be linearly slideable upon an extension 154. In an embodiment, arms 120 and 140 are mirror images of each other, although this is not necessary in order to carry out all aspects of the disclosure. In the embodiment illustrated in FIGS. 1-2, extension 154 has a flattened profile, thereby preventing unintended rotation of arms 120, 140 with respect to each other, and as described below, with respect to arm 160. Other mechanical forms can be provided for extension 154, including for example a cylinder with a key, to enable a like purpose. In an alternative embodiment of the disclosure, any of arms 120, 140, and 160 can be rotated with respect to other of arms 120, 140, and 160, where extension 154 or 170 (described below) is non-keyed, for example cylindrical.

A threaded set screw (not shown), ratchet (shown in other embodiments herein), or other mechanism can be provided to retain arm 120, 140, 160 in a desired linearly translated position. A rack and pinion configuration, not shown in this embodiment, can be provided, formed between extension 154 providing the rack, and with a pinion rotatably free but displaceably confined within arm 120/140 and engaged with the rack. A locking mechanism, for example a set screw or a ratchet mechanism, can be provided to affix extension 154, 170 at a desired displacement.

Arm 160, in this embodiment, includes an arm extension 170 which translates within a slot 172 within a block 174, block 174 connected to extension 154, for example with screws, or by welding, adhesives, or any other known means. In this manner, an orientation of extension 154 maintains a desired or predetermined orientation with respect to slot 172. Accordingly, as arms 120, 140 are translated upon extension 154, or extension segments 154 that are mutually connected, and as arm 160 is translated within block 174, a relative path of arms 120, 140, and 160 is maintained. Further, each arm 120, 140, 160 is independently translatable with respect to the other arms. In this manner, a medical practitioner can retract tissue in a manner which best suits a therapeutic purpose. Arm extension 170 can be provided with an extension stop 178, to prevent an undesired separation of arm 160 from a remainder of retainer 10.

As can be seen in FIGS. 1-2, arms 120, 140 are sized and dimensioned to fit underneath block 174 when arms 120, 140 are approximated. In this manner, an overall dimension of retractor 10 is minimized, thereby reducing a physical obstruction introduced by retractor 10, and maximizing visualization within the surgical site. Arm 160 can be adjusted and affixed in any translated position as described with respect to arms 120, 160 upon extension 154, however a rack would be formed upon extension 170, and a pinion disposed within block 174.

It should be understood that in this embodiment, as well as other embodiments herein, while arms 120, 140 are configured to form a slot, and translate upon an extension, they could be configured to include extensions which translate within a block, as shown for arm 160. Similarly, arm 160 could form a block which slides upon an extension, as shown for arms 120, 140. In one aspect of the disclosure, the relative configuration of arms 120, 140 and arm 160 provides for an optimal packaging and a reduced physical profile, although various permutations of blocks and extensions as described herein can be provided, which can produce a reduced profile in a similar manner.

As can be seen in FIG. 1, blades 300 are aligned relative to each other to form a tube 320. In an embodiment, tube 320 has a tapered end 322, and can function as a cannula. When retractor 100 is deployed, tube 320 can be formed by inserting blades 300 into an incision or opening in a patient's body, or can be positioned cooperative with other cannulae, to progressively increase a size of an opening in a body sufficient to admit passage of tube 320 with a minimum of disturbance to body tissue. As body tissue relaxes, or when desired, blades 300 can be separated or moved apart by moving arms 120 and 140 relatively apart. The relative extent of movement of arms 120, 140 do not have to be uniform, and at different times, enabling the medical practitioner to control a timing and extent of force exerted upon different portions of body tissue relative to each blade 312, 314. Similarly, blade 316, in connection with arm 160, can be moved before, during, or after movement of either of arms 120, 140, to be closer or further from blades 312, 314.

As blades 312, 314, and 316 are moved relatively apart, a perimeter defined by an exterior surface of blades 312, 314, and 316 is increased, moving body tissue apart, and increasing access to an area within the body. A greater or fewer number of arms 120, 140, and 160 can be provided upon retractor 10 in a like configuration as arms 120, 140, or 160, each configured to move independently of all other arms.

As can be seen in FIG. 2, blades 312, 314, and 316 can be pivoted to be angled or pitched with respect to their respective arms 120, 140, 160. In this manner, distal ends 330 of blades 300 can be further separated, and the perimeter defined by the exterior surface of the blades can be enlarged, without a necessity of increasing an overall profile of retractor 10, or moving arms 120, 140, 160 any further apart.

FIG. 1 depicts retractor 10 in a "closed" or non-retracted configuration, in accordance with one embodiment of the present disclosure. In the closed configuration, blades 312, 314, and 316 are radially disposed around a central bore 324 to form the substantially closed, tube-shaped structure 320. FIG. 2 depicts retractor system 10 in an "open" or retracted configuration, in which blades 312, 314, 316 have been pitched by being pivoted about a pivot 210 connected to a proximal end 332 of a blade 300, and to an arm 120, 140, or 160. In the open configuration, blades 300 no longer form a tube-shaped structure that is substantially closed.

Blades 300 can each be independently pitched or translated, and can be independently pitched or translated with respect to other blades. A stop element 212, in the embodiment shown, a flange, extends from blade holder 200 and contacts arm 120, 140, or 160 at a desired extreme range of pivoting motion of blade holder 200 and associated blade 300. A screw (not shown) can be provided within aperture 214, which may be threaded, the screw configured to bear upon arm 120, 140, or 160 to cause pivoting of blade holder 200, or to function as a stop element operative to change a maximum range of pivoting motion. Alternative embodiments are described with respect to FIGS. 5-6 and 15, elsewhere herein.

Blade holder 200 is provided with a blade engagement profile 240 extending between opposing ends of blade holder 200. Blades 300 are provided with a blade holder profile 340 mateable with blade engagement profile 240, whereby when profiles 240, 340 are mated, blade 300 can be retained upon blade holder 200 and be slideable along a length of blade holder profile 340 so that a penetration of blade 300 with respect to a patient is adjustable. Further, blades 300 can be replaced with blades having a different shape, size, or tissue engaging profile. In one embodiment, blade holder profile 340 and blade engagement profile 240 form a dovetail connection.

Additionally, blades 300 can be inserted after retractor 10 is fixed in a position with respect to a patient, whereby a blade can be slid upwards and away from the patient, and replaced, without a requirement to move retractor 10 or the patient. In this embodiment, blade holder profile extends to a distal end 330 of blade 300, or blade holder profile is configured to no longer provide a mating engagement along one or more portions of a length of blade 300.

Blades 300 are affixed at a desired displacement along the length of blade holder profile 340 by a friction fit between blade holder profile 340 and blade engagement profile 240, or by a set screw or other fastener (not shown) connected to blade holder 200 and contactable with blade 300 or blade holder profile 340.

Blades 300 can be provided with one or more docking pin slots 350 sized and dimensioned to accept a docking pin (not shown), which can be used to secure a blade 300 in a position with respect to body tissue through which a pin is extended, for example into a vertebra. As all blades engaged upon retractor 10 are mutually connected, each docking pin thus inserted contributes to the overall stabilization of retractor 10.

In an embodiment, retractor 10 is configured for an anterior approach to the spine of the patient. In this embodiment, shown in FIGS. 1-2, arms 120, 140 support caudal oriented blades, and arm 160 supports a cranial oriented blade. A range of pitch motion for blades 300 can include 0 degrees (forming tube 320) to 20 degrees, although substantially larger angulation can be provided, for example 30, 40, or 50 degrees, or a greater range of angulation.

In surgical procedures where imaging is to take place, for example X-ray imaging, it is advantageous if at least blades 300 of retractor 10 are at least partially radiolucent, to foster visualization of the imaged area. Accordingly, blades 300 can be fabricated using aluminum, carbon fiber, or polymeric materials, or any other sufficiently strong and radiolucent material, or combination of materials, which is known or hereinafter developed.

With reference to FIGS. 3-6, in an alternative frame embodiment 100A of the disclosure, retractor 10A includes elements similar to those of the embodiment of FIGS. 1-2, and bears similar reference numbers. In FIGS. 3-4, arms 120A, 140A, and 160A support blades 300 in a manner similar to arms 120, 140, and 160 of FIGS. 1-2, but arms 120A, 140A form square or rectangular channels which translate upon extensions 154A. Similarly, arm 160A translates within a rectangular channel forming block 174A. Keys 180, 182, and 184 are positioned to be rotated by a medical practitioner while retractor 10A is deployed, thereby translating arm 120A, 140A, or 160A. With additional reference to FIGS. 5-6 and 11, each of keys 180, 182, and 184 are connected to a pinion (not shown) rotatably fixed to arm 120A, 140A for keys 180, 182, and to block 174A for key 184. A toothed rack 186 is formed upon a side surface of each extension 154A, and a similar toothed rack 188 is formed upon a side surface of arm 160. In this manner, rotation of key 180, 182, or 184 causes a corresponding translational movement of arm 120A, 140A, and 160A, respectively. In FIG. 4, keys 180 and 182 have been rotated to separate arms 120A, 140A, and key 184 has been rotated to retract arm 160A.

In FIGS. 5-6, as can be seen in frame embodiment 100B, in place of keys 180, 182, and 184, tool engagements 190, 192, 194 are connected to rotatably fixed pinions mateable with racks 186, 188. Tool engagements 190, 192, and 194 are engageable by a driving tool, such as a hex or allen head driver. Accordingly, a driving tool (not shown) can be rotated by a hand of a medical practitioner, or by an electrical or computer controlled actuator, to adjust a position of arms 120B, 140B, or 160B, and thereby change a position of one or more blades 300, including for example blades 312, 314, or 316. It should be understood that either a key 180 configuration, or a tool engagement 190 configuration, as shown in FIGS. 3-6, can be provided in the embodiment of FIGS. 1-2.

With further reference to FIGS. 5-6, a blade pitch tool engagement 230, 232, 234 is provided, rotatable using a tool as described with respect to tool engagements 190, 192, and 194, and operative thereby to change a pitch of a blade 300 attached to blade holder 200.

More particularly, in one configuration, blade holder 200 is pivotally mounted at pivot 210, and blade pitch tool engagement 230, 232, and 234 are each rotatably retained upon their respective blade holder 200. Threaded shaft 236 is keyed to prevent rotation, but is axially displaceable by rotation of blade pitch tool engagement 230, 232, 234. As a result, shaft 236 can be caused to bear against arm 120B, 140B, 160B to cause rotation of blade holder 200 about pivot 210, and to thereby change an angle of blade 300. In another embodiment, blade pitch tool engagement 230, 232, 234 is affixed to shaft 236, and shaft 236 is threadably received within blade holder 200. Thus, as blade pitch tool engagement 230, 232, 234 is rotated, shaft 236 bears against its respective arm 120B, 140B, 160B. In a variation of this embodiment, shaft 236 is threadably received within arm 120B, 140B, 160B. Other variations, including a threaded blade holder 200, can be provided. In any of the foregoing embodiments, a biasing element (not shown) can be provided to bias blade holder 200 in a closed or pitched position, where a position of blade holder 200 is not positive controlled in each direction of rotation about pivot 210. It should be noted that in one embodiment, the blade holder 200 may be positively controlled in each direction about the pivot 210. While not shown for all embodiments, it should be understood that the foregoing blade holder pitch mechanism described for FIGS. 3-6 can be provided for other embodiments herein.

Figure 15:
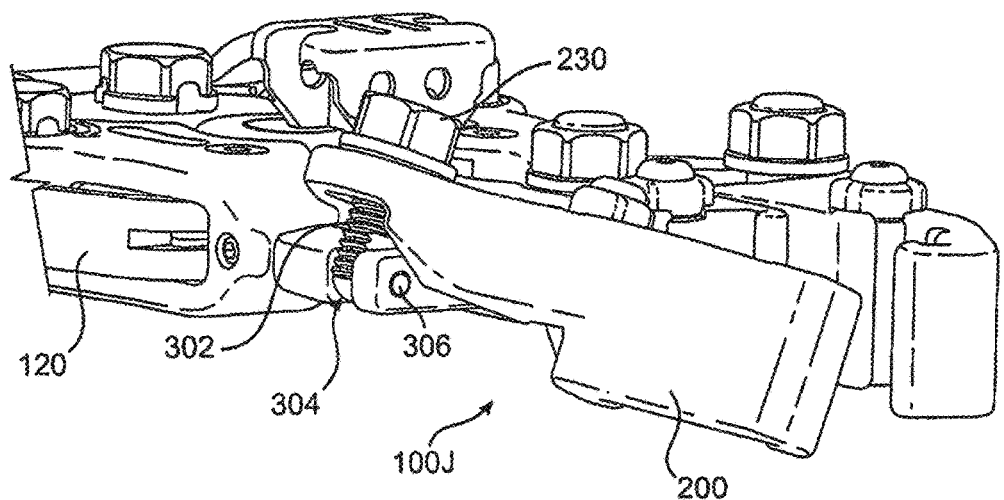
FIG. 15 depicts an alternative blade pitch mechanism of the disclosure.

FIG. 15 illustrates an alternative embodiment, including frame 100J, for controlling blade pitch. More particularly, changing an angulation or pitch of blade holder 200 is accomplished by rotating blade pitch tool engagement 230, which has an attached threaded shaft 302, within a corresponding threaded receiver 304 pivotally connected to blade holder at pin 306.

Blade pitch tool engagement 230, 232, or 234 can be engaged with a tool, for example an allen or hex wrench, or may be provided with a knurled nut or manually engageable key. In this configuration, blade 300 can be pitched at a theoretically infinite range of angles. Other embodiments can be provided wherein blade 300 can be pitched at discrete stop points. A tool thus engaged can also be used to manipulate all or portions of retractor 10, or a separate tool engagement can be provided upon retractor 10 to enable manipulation of other components of retractor 10 described herein.

With further reference to FIGS. 5-6, a ratcheting pawl 250 can be provided, pivotable about pawl pivot 252, a pawl 250 provided for any or all actuators having a toothed rack, including arms 120B, 140B, and 160B, and all other embodiments herein upon which a rack is formed. A pawl tooth 254 has a sloped surface configured to allow rack 186, 188 to pass in one direction, but not an opposite direction. In the embodiment shown, pawl 250 enables arms 120B, 140B, and 160B to move apart, relative to each other. This operates to maintain tissue retracted during a therapeutic procedure. When the procedure is complete, or it is desired to otherwise remove retractor 10, pawl 250 can be rotated about pivot 252 to disengage pawl tooth 254 from rack 186, 188, whereupon key 180, 182, and 184, or tool engagement 190, 192, or 194 can be rotated to change a position of its associated arm.

In an alternative embodiment, pawl 250 does not include a sloped surface at pawl tooth 254, and accordingly the pawl must be retracted from contact with rack 186 or 188 to enable movement of the associated arm.

FIGS. 5-6 further illustrate a frame mount 142, which enables frame 100 (or frame 100A, 100B, and other frame embodiments herein) of retractor 10 to be mounted to a table or other supporting structure with a single mounting point. A support coupling 450 is affixed to the supporting structure with a rod (not shown) threadably or otherwise securable within an end of coupling 450. Coupling 450 includes a threaded rod 148 and nut 148A extending from an end portion. Coupling 450 is inserted into chamber 144 of frame mount 142, and the attached threaded rod is passed into notch 146. Nut 148A is tightened to secure coupling 450 to frame mount 142, and thereby securing retractor 10 to a supporting structure. The frame mount 142 illustrated includes two notches 146, thereby enabling a support coupling to be connected to either side, or to both sides, of frame mount 142. Two or more frame mounts 142 can be provided, as illustrated in FIGS. 7-9, providing multiple or alternative mounting points for retractor 10. In FIGS. 7-9, it may be seen that arm extension 160D is connected to arm 160C using a similar attachment mechanism.

With further reference to FIGS. 5-6, a cam latch 220 is rotatably retained upon blade holder 200, and is oriented to engage a slot (not shown) within blade 300. In this manner, blade 300 is releasably retained upon blade holder 200, and is prevented from sliding within blade holder profile 340. Alternatively, cam latch 220 can overlap a protrusion (not shown) formed upon blade 300.

The embodiment of FIGS. 7-9 is analogous to the embodiment of FIGS. 1-2 and 3-6, however arms 120C, 140C include arm extensions 120D, 140D, and arm couplings 430 and 432. In one embodiment, rotation of coupling blade pitch tool engagements 430, 432 are configured to change a pitch of blades 312, 314 in a similar manner as described with respect to blade pitch tool engagements 230, 232. However, by positioning the corresponding pitch actuating components proximal with respect to blades 300, less structure is imposed upon the target therapy site, improving visualization and manipulation within the target zone. Blade holders 200D are configured to be compact, particularly as articulation does not need to be supported near a blade 300 attachment.

In an alternative embodiment, engagements 430, 432 are coupled to pinions which rotate upon a rack formed in arm 120C or 140C. Thus, rotation of engagements 430, 432 extend or retract arm extensions 120D, 140D. Alternatively, engagements 430, 432 enable articulation of arm extensions 120D, 140D when rotated in one embodiment, and when loosed and manipulated in another embodiment. Articulation can be carried out by pivoting arm extension 120D, 140D about a pivot defined by engagement 430, 432, respectively.

Figure 16:
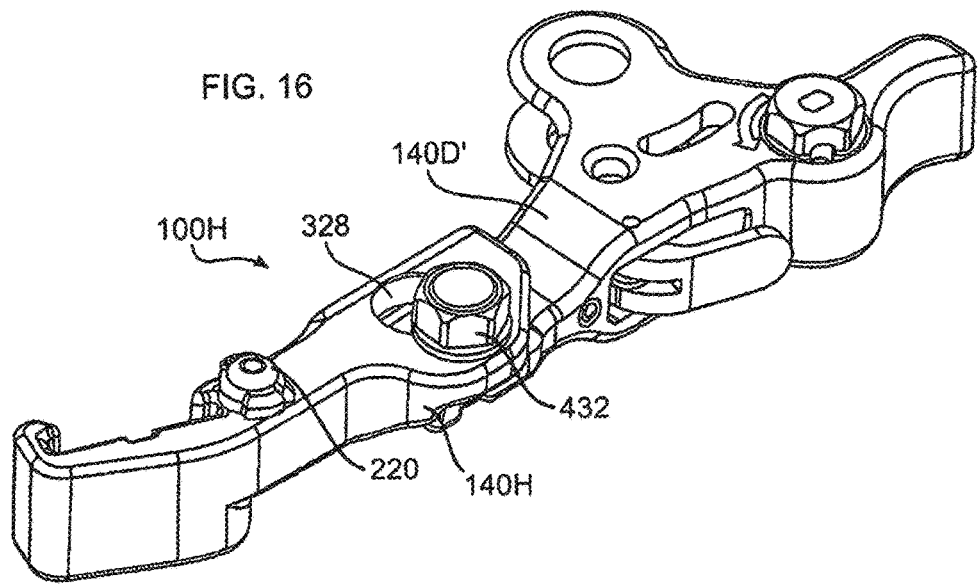
FIG. 16 depicts an articulated blade holding arm in accordance with the disclosure.

In a yet further embodiment, couplings 430, 432 enable rapid replacement of arm extensions 120D, 140D. In a yet further embodiment, engagements 430, 432 are connected to threaded shafts (not shown), which lie within elongated slots 328. In this manner, arm extensions 120D, 140D can be displaced laterally with respect to arms 120C, 140C. In a variation of this embodiment, arm extensions 120D, 140D can be pivoted after lateral displacement within elongated slots 328. An embodiment frame 100H having elongated slots 328 disposed within arm 140D' and arm extension 140H is shown in FIG. 16.

With reference to FIG. 10, an embodiment of a retractor 10 of the disclosure includes a frame 100E combining various elements described elsewhere herein, as indicated, and further includes thumbwheels 260 for changing a relative offset of arms 120E, 140E. In an embodiment, a pinion (not shown) rotatably connected to thumbwheel 260 engages rack 186 to cause movement of arm 120E or 140E relative to extension 154E.

As can further be seen in FIG. 10, an additional moveable extension 170A is provided with a rack 188A and pinion (not shown) controllable, in this example, with a key 184A. A mounting block 288 is connected to block 174, whereby extension 170A can be moved independently of extension 170, and arm 188. In an embodiment, extension 170A is connected to a supporting structure, frame 100E moveable with rotation of key 184A.

Figure 11:
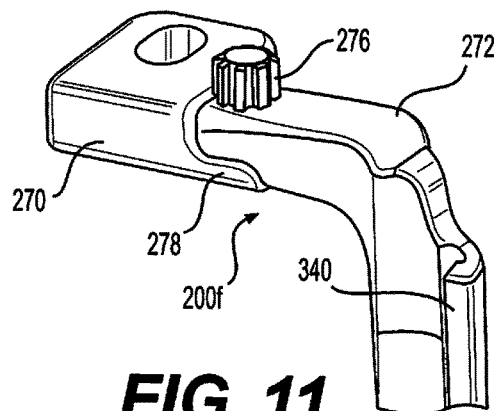
FIG. 11 depicts a blade mounting configuration of the disclosure.
Figure 12:
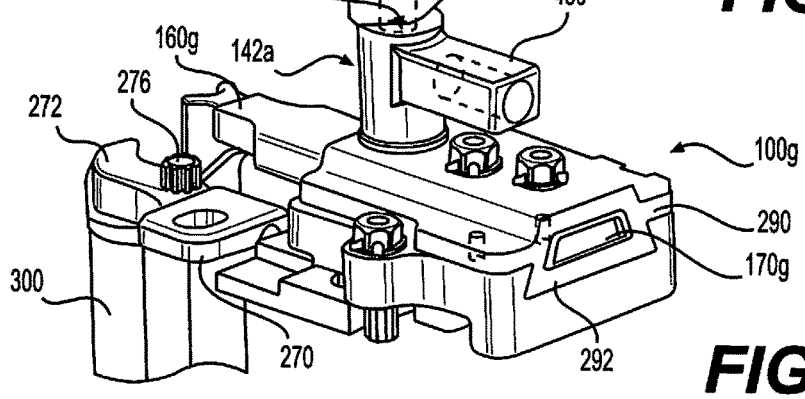
FIG. 12 depicts the blade mounting configuration of FIG. 11, connected to a retractor of the disclosure, the retractor configured with an alternative frame mount of the disclosure.

With reference to FIGS. 11-12, a compact blade holder 200F includes a mounting block 270 extending from or affixable to a remainder of retractor 10 using any known method. Block 270 includes a chamber 274 sized to receive a mounting holder extension 272. A set screw 276 is threadably retained within holder extension 272, and bears against a block flange 278 when extension 272 is inserted within chamber 274 and set screw 276 is tightened. Alternatively, set screw 276 can be threaded into block flange 278. In this manner, mounting holder extension 272 is releasably securable within block 270, and is thereby attachable to retainer 10. A blade engagement profile 240 extends from holder extension 272, and is connectable to a blade 300 as described with respect to FIGS. 1-2. In an alternative embodiment, blade 300 forms holder extension 272, and therefore is directly attachable to block 270 as described above.

Referring now to FIG. 12, frame mount 142A includes a central bore 280 through which a threaded screw 282 (not shown) can be passed, to threadably engage frame 100. In this manner, frame mount 142A can be rotated about an axis defined by bore 280 to a desired orientation. In this embodiment, a key 284 is connected to screw 282, and can be rotated to tighten screw 282 and thereby affix a position of frame mount 142A relative to frame 100.

In the embodiment of FIG. 12, screw 282 threadably engages a slideable block that is retained within frame 100G with a dovetail connection 292, and is thereby longitudinally positionable within frame 100. Extension 170G of arm 160G is slideably retained within slideable block 290, and may be adjusted within block 290 using any of the methods disclosed elsewhere herein, including a rack and pinion configuration. In the embodiment shown, pinch bolts 294 can be rotated to tighten or loosen extension 170G.

Figure 13:
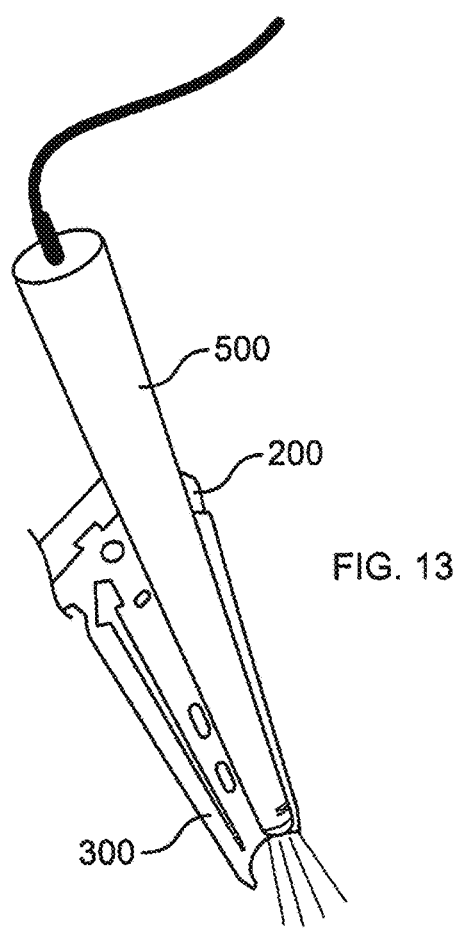
FIG. 13 depicts a light source retained by a blade holder of the disclosure.

Referring now to FIG. 13, a light source 500 can be affixed to blade 300, or to blade holder 200. Light source 500 can be provided with a blade holder profile 340 mateable with a blade engagement profile 240 of blade holder 200. Alternatively, light source 500 can be affixed to blade holder 200 or blade 300 using any known means, including for example magnetic, hook and loop fastener, threadable faster, resilient attachment means, or adhesive. A target of focus of light emitted from light source 500 can be adjusted by changing a pitch of blade holder 200, or by translating an associated arm 120, 140, 160, as needed.

Figure 14:
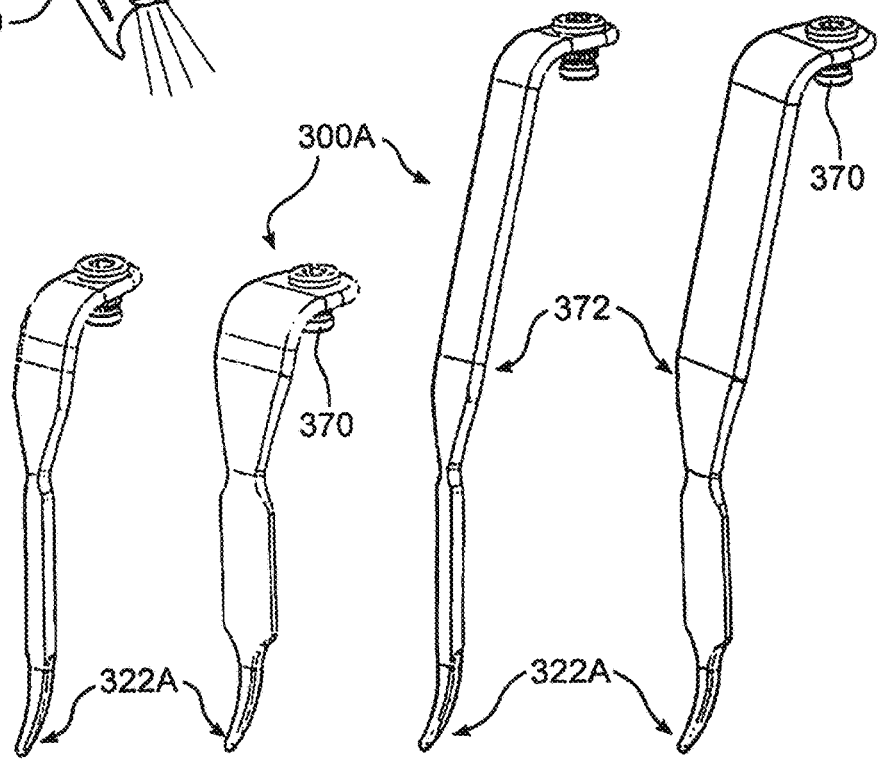
FIG. 14 depicts an alternative blade type, and an alternative blade mounting configuration, of the disclosure.

With reference to FIG. 14, a variety of blade shapes 300 can be employed together with retractor 10 of the disclosure. In addition, while blades 300 can be provided with a blade holder profile, as illustrated in FIGS. 1-2, blades 300 can alternatively be configured with a splined shaft 370, which can be mateable with a corresponding receiver provided upon blade holder 200 to secure retain blade 300, and to prevent rotation. In this manner, a wide variety of blade 300 styles and blade attachment mechanisms may be employed together with the various embodiments of the disclosure. In FIG. 14, blades 300A are configured to engage bone of the body, for example vertebrae. Blades 300A include are angled at 372 to enable mounting blocks 200 to be positioned further from the target surgical zone, and are further provided with tapered ends 322A which securely engage and retain bone. Accordingly, blades 300A do not form a tube 320 in this embodiment. It may also be seen that blades 300/300A can be provided in various lengths, widths, and if tubes 320 are formed, various lengths and diameter tubes. Blades 300/300A can be provided in a variety of sizes, including for example 8 mm to 18 mm wide, and lengths from 110 mm to 200 mm, although substantially narrower, wider, shorter, or longer blades can be provided. Although two blade types are illustrated herein, a wide variety of blade types, styles, sizes and lengths can be used in accordance with the disclosure.

Figure 17:
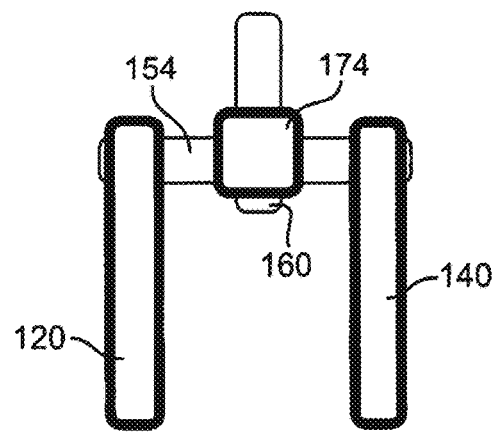
FIG. 17 is a diagram of the operative configuration of the retractor of FIGS. 1-2, in an open configuration.
Figure 18:
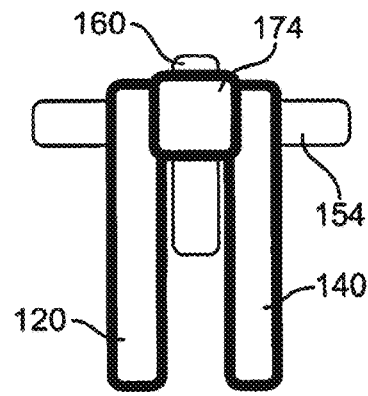
FIG. 18 depicts the retractor of FIG. 17, in a closed configuration.
Figure 19:
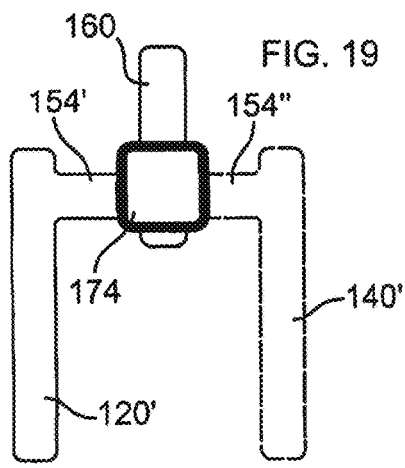
FIG. 19 is a diagram of an alternative retractor of the disclosure, in an open configuration.
Figure 20:
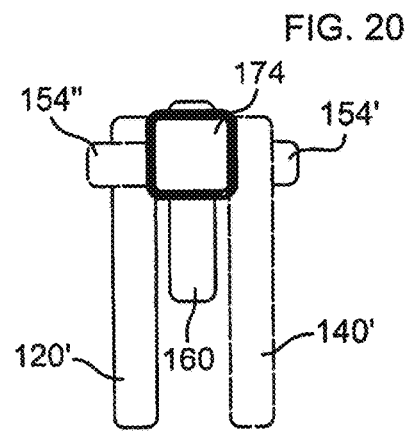
FIG. 20 depicts the retractor of FIG. 19, in a closed configuration.
Figure 21:
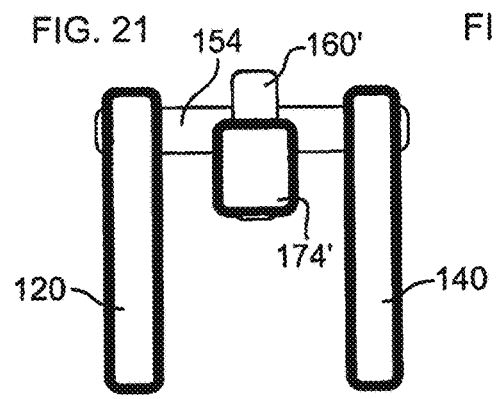
FIG. 21 is a diagram of another alternative retractor of the disclosure, in an open configuration.
Figure 22:
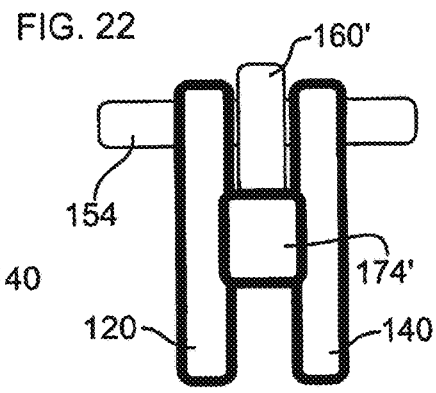
FIG. 22 depicts the retractor of FIG. 21 in a closed configuration.

FIGS. 17-22 diagrammatically illustrate three possible embodiments for carrying out the disclosure, wherein heavy outline represents a block into which an extension is slideable. In FIGS. 17-18, the embodiment of FIGS. 1-2 is depicted, wherein block 174 is affixed to extension 154, thereby forming a fixed core. The remaining components, arms 120, 140, and 160, are slideable independently of each other upon and within the core. In FIGS. 19-20, extensions 154' and 154" extend from arms 120' and 140'. Extensions 154', 154", and 160 slide at different height offsets within block 174, which alone forms the core within which the moveable arms slide. In FIGS. 21-22, arms 120 and 140 form blocks, as in FIGS. 17-18, and arm 160 is formed as a block 174', slideable upon extension 160', which is affixed to extension 154, extensions 160' and 154 forming a core upon which the moveable arms slide. It should be understood that only a single arm 120 or 140 can be provided, or that multiple arms 120 or 140, or multiple arms 160 can be provided, as benefit the therapeutic needs of the patient.

Frame 100 and its constituent components (including variants 100A-100H) may be fabricated from any one or more, or combinations of, metals, polymers, carbon fiber or other composites, natural materials, or any other materials having sufficient strength, durability, and biocompatibility. Materials selected can be radiolucent or radiopaque, as desired.

In accordance with the disclosure, a single mounting location for a frame 100 of the disclosure enables a posterior blade (e.g. 316) to be indexed without moving the cranial caudal blades (e.g. 312, 314), as well as allowing the cranial caudal blades to be indexed without moving the posterior blade.

FIGS. 23-31 depict different views of an alternative retractor system in accordance with some embodiments. The retractor system 610 includes a number of features as in prior embodiments, including first, second, and third blades 612, 614, 616; first, second, and third arms 620, 640, 660; and various engagement mechanisms for independently translating the various blades and arms. The retractor system 610 also includes a number of novel features including a carriage actuator 672 and a third (e.g., posterior) blade actuator 674 that provides different advantages during a surgical procedure, as discussed in more detail below.

Figure 23:
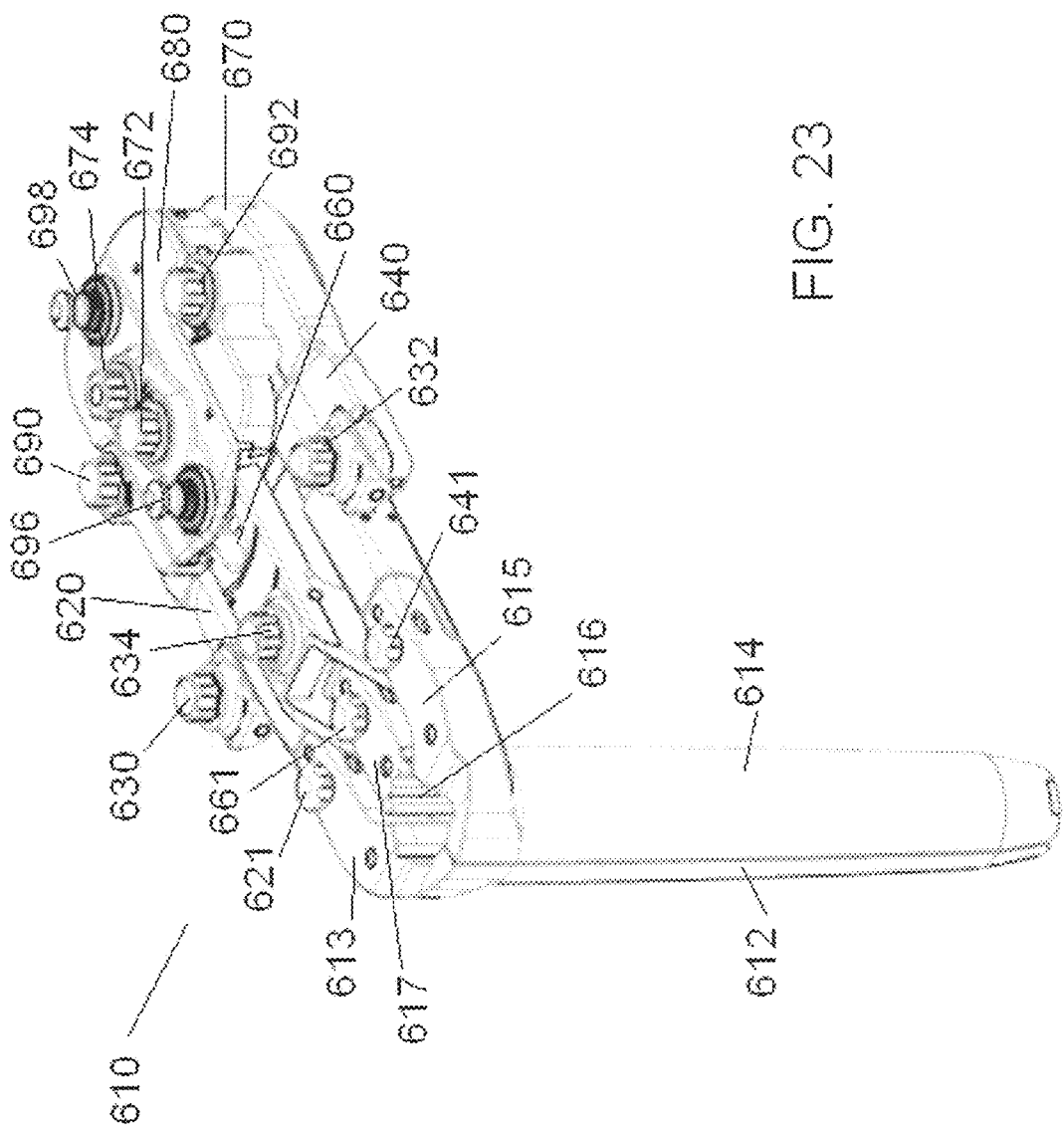
FIG. 23 depicts an alternative retractor system in a closed configuration in accordance with some embodiments.

FIG. 23 depicts an alternative retractor system in a first or closed configuration in accordance with some embodiments. The retractor system 610 comprises a frame including a first arm 620, a second arm 640 and a third arm 660 for holding and attaching one or more blades thereto. A first blade 612 having a first blade arm 613 attaches to the first arm 620. A second blade 614 having a second blade arm 615 attaches to the second arm 640. And a third blade 616 having a third blade arm 617 attaches to the third arm 660. The first blade arm 613 attaches to the first arm 620 via first fastener 621. The second blade arm 615 attaches to the second arm 640 via second fastener 641. The third blade arm 617 attaches to the third arm 660 via third fastener 661. In some embodiments, the first and second blades 612, 614 can be considered cranial caudal blades in view of their direction of movement, while the third blade 616 can be considered a posterior blade.

The retractor system 610 is in a first or closed configuration whereby each of the blades 612, 614, 616 are adjacent one another. The retractor system 610 can advantageously be delivered into a patient in the closed configuration through an open, mini-open or minimally invasive incision. Once in the patient, each of the blades 612, 614, 616 is capable of angulation to thereby expand and retract tissue. Furthermore, each of the arms 620, 640, 660 (and their associated blades) are capable of movement (e.g., translational) in one or more directions, to thereby expand and retract tissue. In some embodiments, one or more blades 612, 614, 616 are angulated away from one another. In other embodiments, one or more blades 612, 614, 616 are translated away from one another. In other embodiments, one or more blades 612, 614, 616 are both angulated and translated away from one another. By separating the blades via angulation or translational movement, this creates a second or open configuration.

Each of the blades 612, 614, 616 is capable of angulation. Advantageously, each of the blades 612, 614, 616 has its own individual mechanism to provide angulation, such that each blade can be angulated independently from one another. A first blade pitch tool engagement or blade angle actuator 630 angulates first blade 612. A second blade pitch tool engagement or blade angle actuator 632 angulates second blade 614. A third blade pitch tool engagement or blade angle actuator 634 angulates third blade 616. In some embodiments, the blade angle actuators 630, 632, 634 are angulated by hand and/or an instrument. In some embodiments, each of the blade angle actuators 630, 632, 634 resides within a base plate. In some embodiments, the base plates pivot around an axis, thereby accommodating the movement caused by the actuators 630, 632, 634.

Each of the arms 620, 640, 660 is capable of movement, such as translational movement. First arm 620 is capable of linear movement via rotation of first tool engagement or linear actuator 690. The first linear actuator 690 can be rotated by hand and/or instrument. As the first linear actuator 690 is rotated, the lower portion of the actuator 690 engages teeth 691 (shown in FIG. 24) as part of a rack and pinion system, thereby advantageously causing the first arm 620 to linearly translate. In some embodiments, rotation of the first linear actuator 690 causes the first arm 620 to move laterally outward (e.g., away from a longitudinal axis that extends through the system frame), thereby separating the first arm 620 from the second arm 640 and third arm 660. Rotation of the first linear actuator 690 in an opposite direction causes the first arm 620 to move laterally inward (e.g., toward a longitudinal axis that extends through the system frame), thereby bringing the first arm 620 closer to the second arm 640 and third arm 660.

Likewise, second arm 640 is capable of linear movement via rotation of second tool engagement or linear actuator 692. The second linear actuator 692 can be rotated by hand and/or instrument. As the second linear actuator 692 is rotated, the lower portion of the actuator 692 engages teeth 693 (shown in FIG. 24) as part of a rack and pinion system, thereby advantageously causing the second arm 640 to linearly translate. In some embodiments, rotation of the second linear actuator 692 causes the second arm 640 to translate or move laterally outward (e.g., away from a longitudinal axis that extends through the system frame), thereby separating the first arm 620 from the second arm 640 from the first arm 620 and third arm 660. Rotation of the second linear actuator 692 in an opposite direction causes the second arm 640 to move laterally inward (e.g., toward a longitudinal axis that extends through the system frame), thereby bringing the second arm 640 closer to the first arm 620 and third arm 660.

In addition to accommodating linear lateral translation of one or more arms (e.g., the first and second arms that attach to the first and second cranial caudal blades), the retractor system 610 can also provide linear translation of one or more arms in a longitudinal direction that runs along a length of the retractor system. In some embodiments, the retractor system 610 comprises a carriage actuator 672 that actuates a moveable carriage 670 to which the first arm 620 and the second arm 640 are attached, thereby causing the first blade 612 and the second blade 614 to translate in a longitudinal or anterior/posterior direction. In some embodiments, the carriage actuator 672 actuates the moveable carriage 670 via a rack and pinion system. In some embodiments, the retractor system 610 further comprises a posterior blade actuator 674 that causes translation of the third arm 660, thereby causing the third blade 616 to translate in a longitudinal or anterior/posterior direction. In some embodiments, the posterior blade actuator 674 actuates the third arm 660 via a rack and pinion system.

In some embodiments, a fixed plate 680 is provided with a moveable carriage or carriage plate 670 positioned thereunder. As shown in FIG. 23, fixed plate 680 comprises an opening for receiving the third arm 660 therethrough. In some embodiments, the third arm 660 is in the form of a dovetail, whereby it forms a dovetail connection with the fixed plate 680. A moveable carriage 670 is positioned on an underside of the fixed plate 680, and is configured to translate while holding the first blade 612 and the second blade 614 via rotation of the carriage actuator 672. On an upper surface of the fixed plate 680, carriage actuator 672 and posterior blade actuator 674 extend therefrom.

Rotation of the carriage actuator 672 causes the carriage 670 to move or translate linearly in a longitudinal or posterior/anterior direction. In some embodiments, the fixed plate 680 remains in place, while the carriage 670 translates relative to the fixed plate 680. As the carriage 670 is attached to both the first arm 620 and the second arm 640, while the first arm 620 is attached to the first blade 612 and the second arm 640 is attached to the second blade 614, movement of the carriage 670 causes translational movement of both the first blade 612 and the second blade 614. Rotation of the carriage actuator 672 in a first direction causes the first and second blades (e.g., the cranial caudal blades) 612, 614 to move away from the third blade (e.g., posterior blade) 616. Rotation of the carriage actuator 672 in a second direction causes the first and second blades (e.g., the cranial caudal blades) 612, 614 to move toward the third blade (e.g., posterior blade) 616.

Rotation of the posterior blade actuator 674 causes the third arm 660 to move or translate linearly in a longitudinal or posterior/anterior direction. As the third arm 660 is attached to the third blade (e.g., the posterior blade) 616, movement of the posterior blade actuator 674 causes translational movement of the third blade 616. Rotation of the posterior blade actuator 674 in a first direction causes the third blade 616 to move away from the first and second blades (e.g., the cranial caudal blades) 612, 614. Rotation of the posterior blade actuator 674 in a second direction causes the third blade (e.g., the posterior blade) to move toward the first and second blades (e.g., the cranial caudal blades) 612, 614.

The carriage actuator 672 and the posterior blade 674 provide unique advantages to the present system. For example, a surgeon may position the retractor system 610 such that the third blade 616 is next to or blocking a nerve (e.g., a femoral nerve), but may want to retract tissue further in a longitudinal direction. Rather than having to move the entire retractor system 610, the present retractor system 610 simply allows the surgeon to rotate the carriage actuator 672, thereby providing translation of the first and second blades 612, 614, without having to move the entire system. In another example, a surgeon may have positioned the retractor system 610 such that the first and second blades 612, 614 are in a desired position, while the third blade 616 has room to be brought closer to a nerve (e.g., a femoral nerve). Rather than having to move the entire retractor system 610, the present retractor system 610 simply allows the surgeon to rotate the posterior blade actuator 674, thereby providing translation of the third blade 616 without having to move the entire system, thus advantageously increasing retractor accuracy and saving time during a surgical procedure.

In some embodiments, the retractor system 610 further includes a first attachment mechanism 696 and a second attachment mechanism 698 for attaching additional components to the frame. Each of the attachment mechanisms 696, 698 extends from an upper surface of the retractor system 610. The attachment mechanism 696, 698 comprise extensions or protrusions for which a component can be attached thereon. As shown in FIG. 23, the first attachment mechanism 696 is positioned closer to the blades 612, 614, 616 than the second attachment mechanism 698. In some embodiments, a fourth arm and/or blade can be attached to the first attachment mechanism 696. In some embodiments, a table mount component can be attached to the second attachment mechanism 698, such that the entire frame with the blades can be attached to a table.

Figure 24:
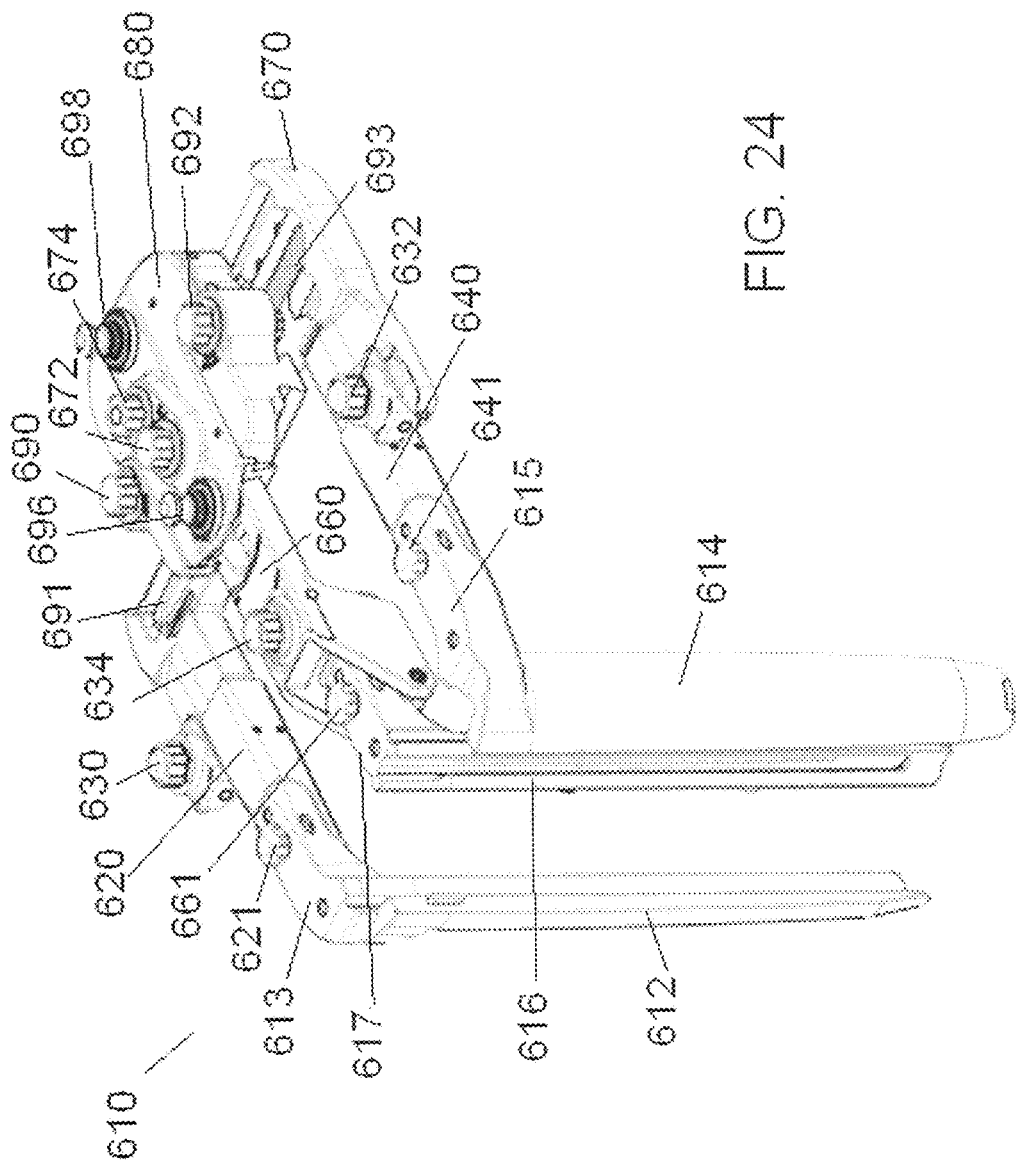
FIG. 24 depicts the retractor system of FIG. 23 in an open configuration in accordance with some embodiments.

FIG. 24 depicts the retractor system of FIG. 23 in a second or an open configuration in accordance with some embodiments. As shown in the figure, the first blade 612, second blade 614 and third blade 616 have been separated apart from one another. In some embodiments, the first linear actuator 690 has been rotated to move or translate the first blade 612 away from the second blade 614 and the third blade 616. Likewise, the second linear actuator 692 has been rotated to move or translate the second blade 614 away from the first blade 612 and the third blade 616. In the open configuration in FIG. 23, the blades provide a greater channel through which one or more instruments and/or implants can be inserted through the retractor system 610.

Figure 25:
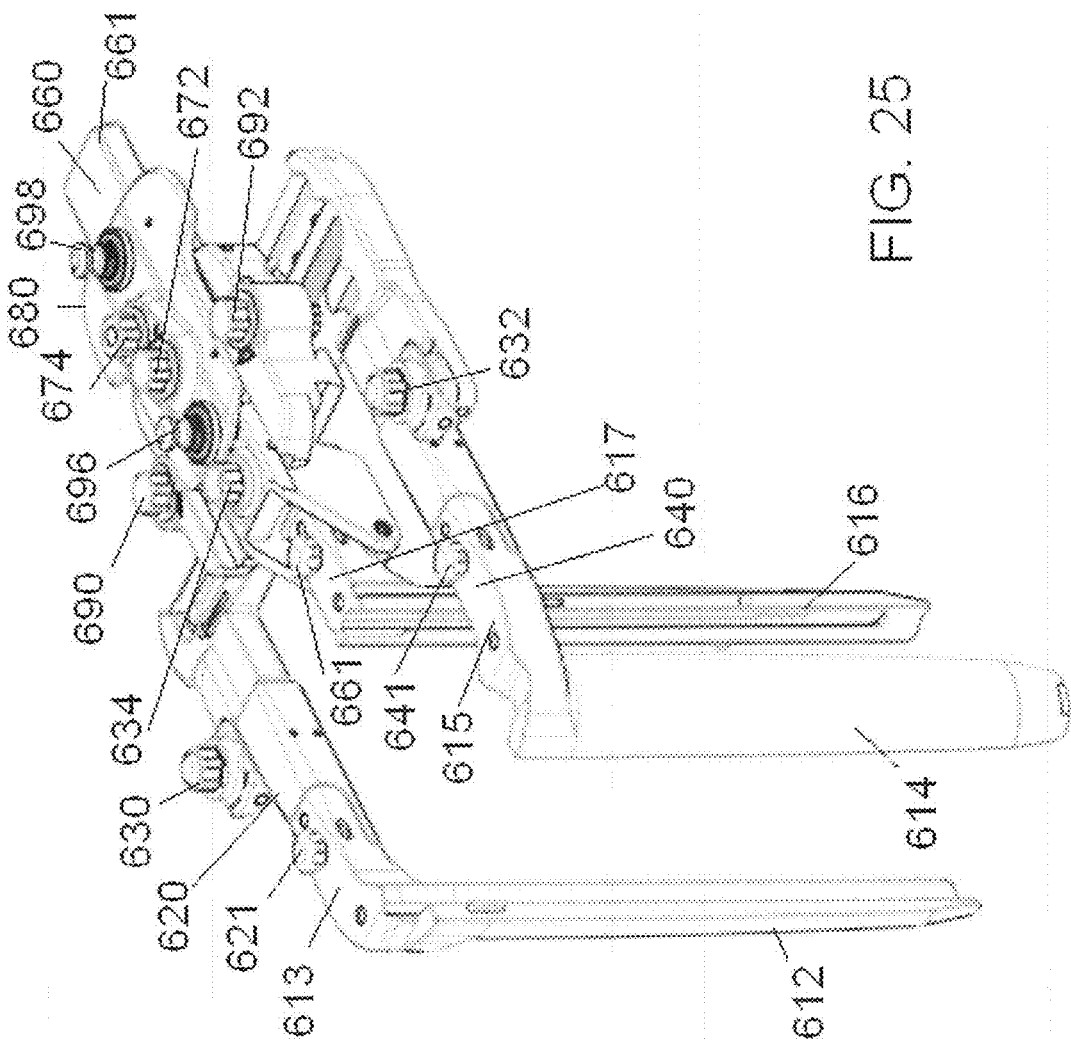
FIG. 25 depicts the retractor system of FIG. 23 in an open configuration with its posterior blade moved in accordance with some embodiments.

FIG. 25 depicts the retractor system of FIG. 23 in a different second or open configuration with its posterior blade moved in accordance with some embodiments. Like the retractor system 610 in the previous figure, the retractor system 610 is in an open configuration whereby the first blade 612, second blade 614 and third blade 616 are separated from one another. The first blade 612 has been moved away from the second blade 614 and the third blade 616 via the first linear actuator 690, while the second blade 614 has been moved away from the first blade 612 and the third blade 616 via the second linear actuator 692. In addition, as shown in FIG. 25, the third blade 616 (e.g., the posterior blade) has been moved linearly away from the first and second blades 612, 614 (e.g., the cranial caudal blades) via posterior blade actuator 674. As shown in the figure, upon rotation of the posterior blade actuator 674, the third arm 660 moves back through the fixed plate 680 of the frame of the retractor system 610, thereby exposing a posterior portion 661 of the third arm 660.

Figure 26:
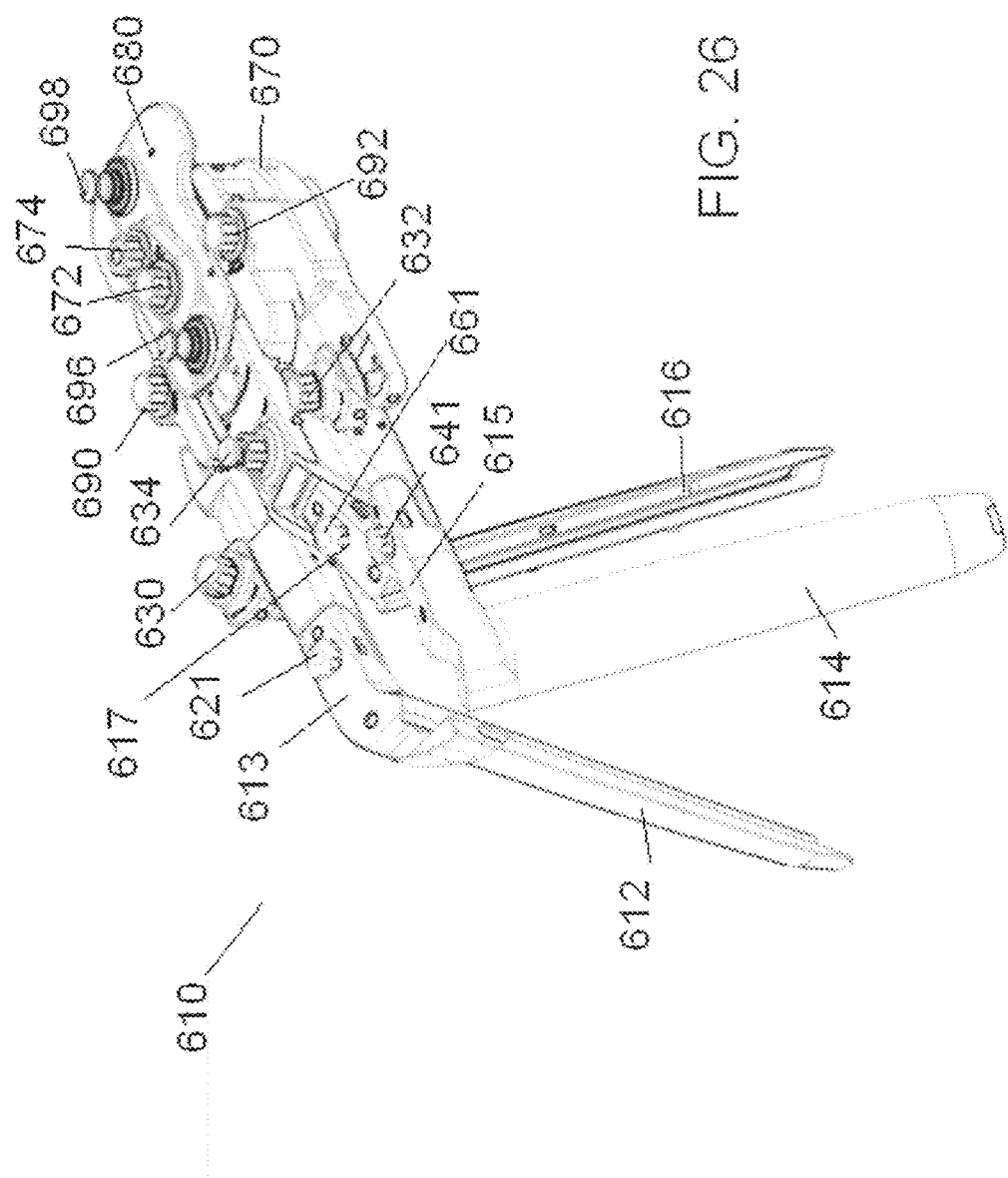
FIG. 26 depicts the retractor system of FIG. 23 in an open configuration with its cranial caudal blades moved in accordance with some embodiments.

FIG. 26 depicts the retractor system of FIG. 23 in a different second or open configuration with its cranial caudal blades moved in accordance with some embodiments. Like the retractor system in FIG. 24, the retractor system 610 is in an open configuration whereby the first blade 612, second blade 614 and third blade 616 are separated from one another. As shown in FIG. 26, the carriage actuator 672 has been rotated such that the carriage 670 attached to the first blade 612 and the second blade 614 has been translated linearly (e.g., in an anterior direction). In other words, the first and second blades 612, 614 (e.g., the cranial caudal blades) have been shifted anteriorly in accordance with some embodiments. From FIG. 26, one can see how the carriage 670 has been shifted relative to the fixed plate 680. In addition, the first blade 612, second blade 614 and third blade 616 have been angulated via blade angle actuators 630, 632 and 634.

Figure 27:
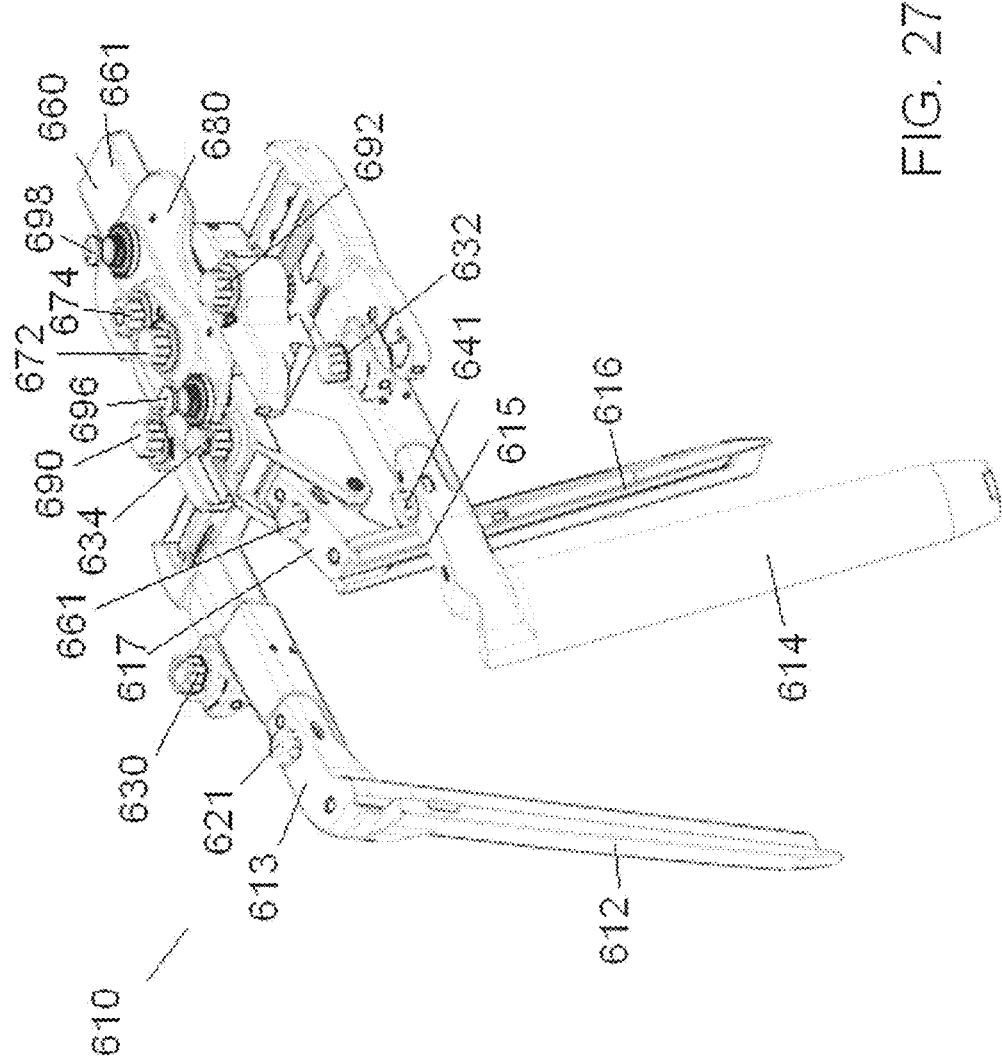
FIG. 27 depicts the retractor system of FIG. 23 in an open configuration with its posterior and cranial caudal blades moved in accordance with some embodiments.

FIG. 27 depicts the retractor system of FIG. 23 in a different second or open configuration with its posterior and cranial caudal blades moved in accordance with some embodiments. Like the retractor system in FIG. 24, the retractor system 610 is in an open configuration whereby the first blade 612, second blade 614 and third blade 616 are separated from one another. As shown in FIG. 27, the carriage actuator 672 has been rotated such that the carriage 670 attached to the first blade 612 and the second blade 614 has been translated linearly (e.g., in an anterior direction). In other words, the first and second blades 612, 614 (e.g., the cranial caudal blades) have been shifted anteriorly in accordance with some embodiments. From FIG. 27, one can see how the carriage 670 has been shifted relative to the fixed plate 680. In addition, the posterior blade actuator 674 has been rotated such that the third blade 616 (e.g., the posterior blade) has been moved linearly away from (e.g., in a posterior direction) from the first blade 612 and the second blade 614. From FIG. 27, one can see how the third arm 660 has been translated linearly such that at least a posterior portion 661 of it is now exposed from the fixed plate 680. In addition, the first blade 612, second blade 614 and third blade 616 have been angulated via blade angle actuators 630, 632 and 634. As shown by each of the configurations in FIGS. 24-27, the blades can have various spacings and angles relative to one another.

Figure 28:
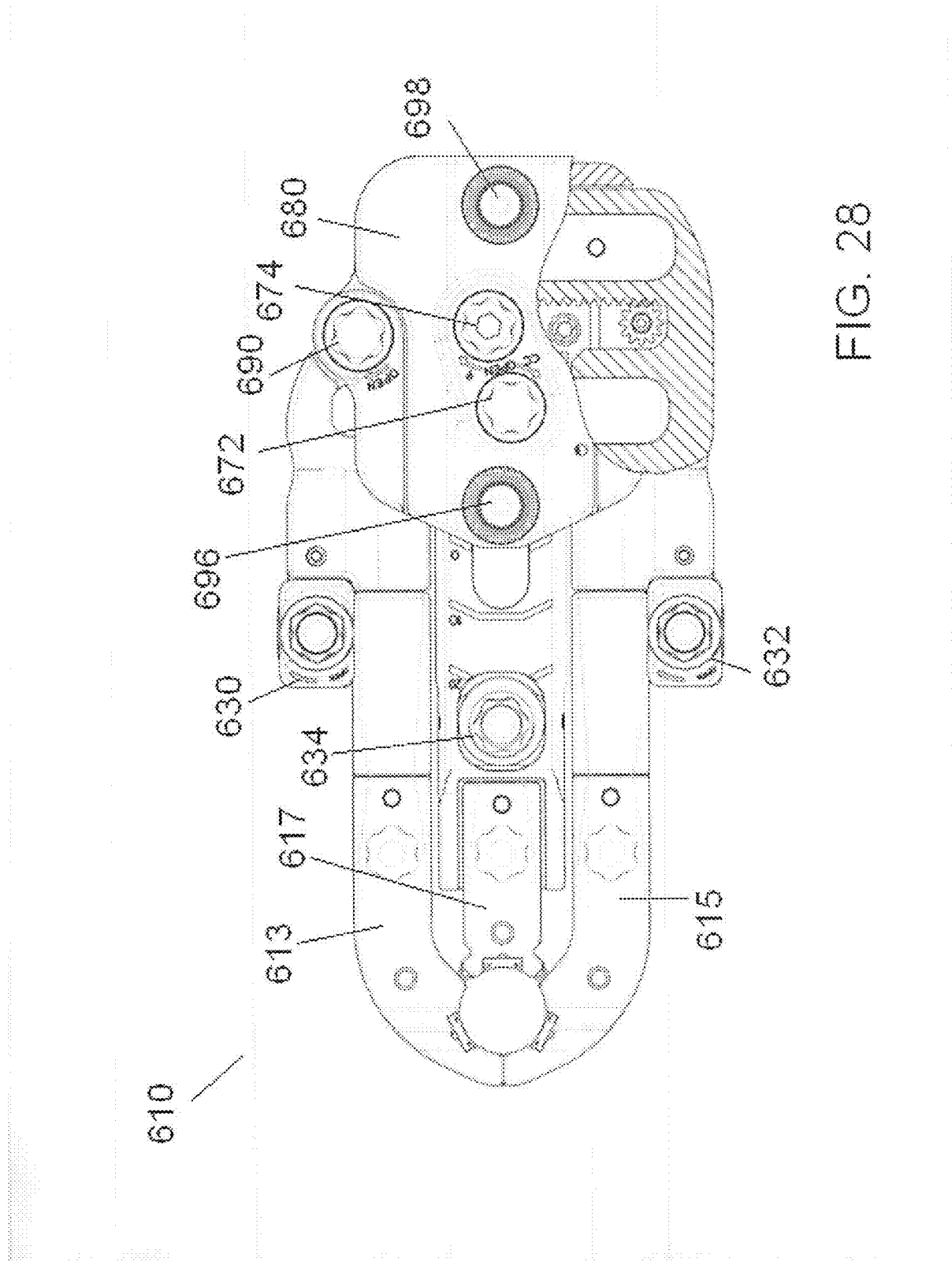
FIG. 28 depicts a top view of the retractor system of FIG. 23 in accordance with some embodiments.
Figure 29:
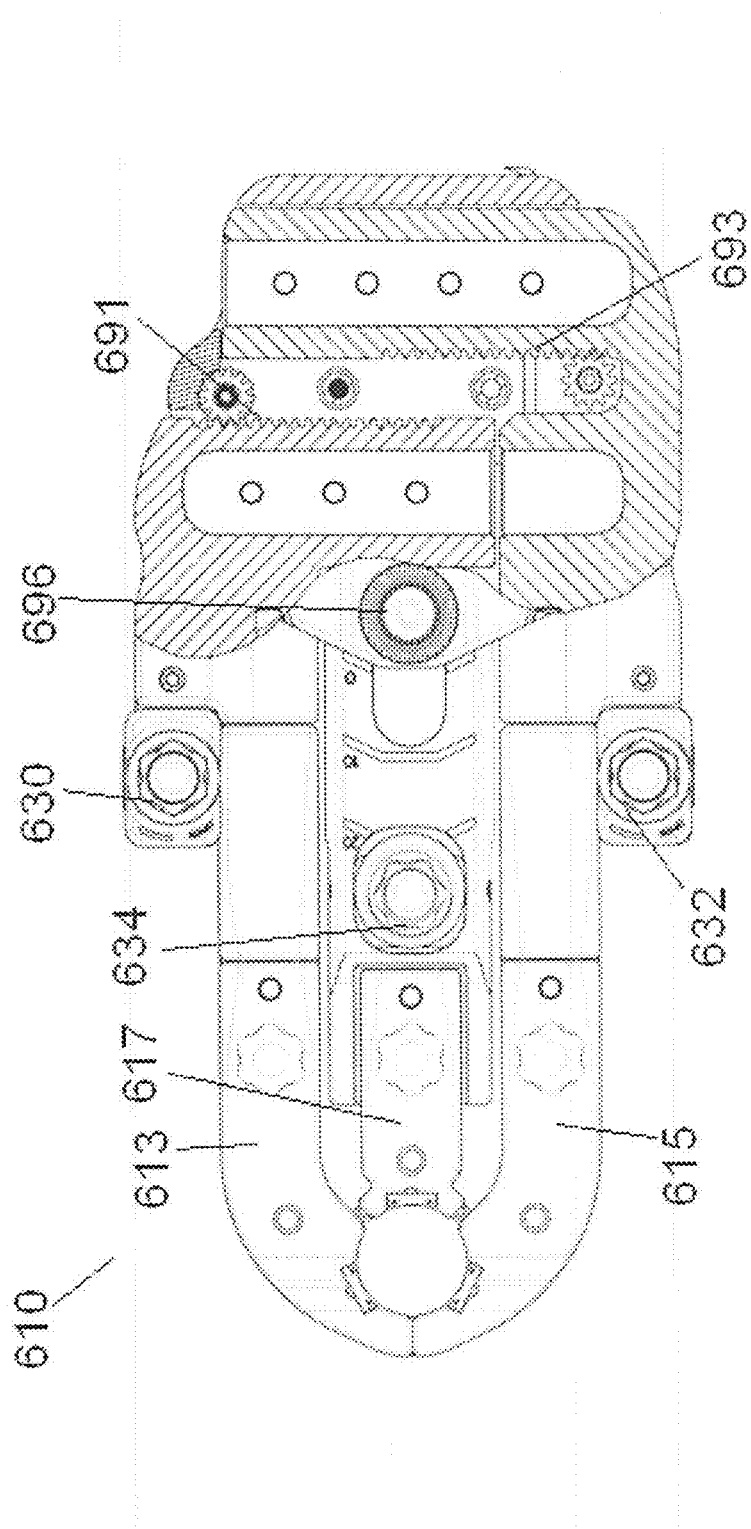
FIG. 29 depicts a top view of the retractor system of FIG. 23 with the fixed plate removed in accordance with some embodiments.

FIGS. 28 and 29 depict top views of the retractor system of FIG. 23 in accordance with some embodiments. FIG. 28 shows the retractor system 610 with the fixed plate 680, while FIG. 29 shows the retractor system 610 with the fixed plate 680 removed. From these views, one can see how the various actuators and knobs actuate and translate the arms and blades of the retractor system. For example, one can see how rotation of the first linear actuator 690 causes a bottom gear portion of the actuator 690 to engage teeth 691 (shown in full view in FIG. 29), thereby causing the first arm 620 and first blade 612 to linearly translate. Rotation of the second linear actuator 692 likewise engages a different set of teeth 693 (shown in full view in FIG. 30), thereby causing the second arm 640 and second blade 614 to linearly translate.

Figure 30:
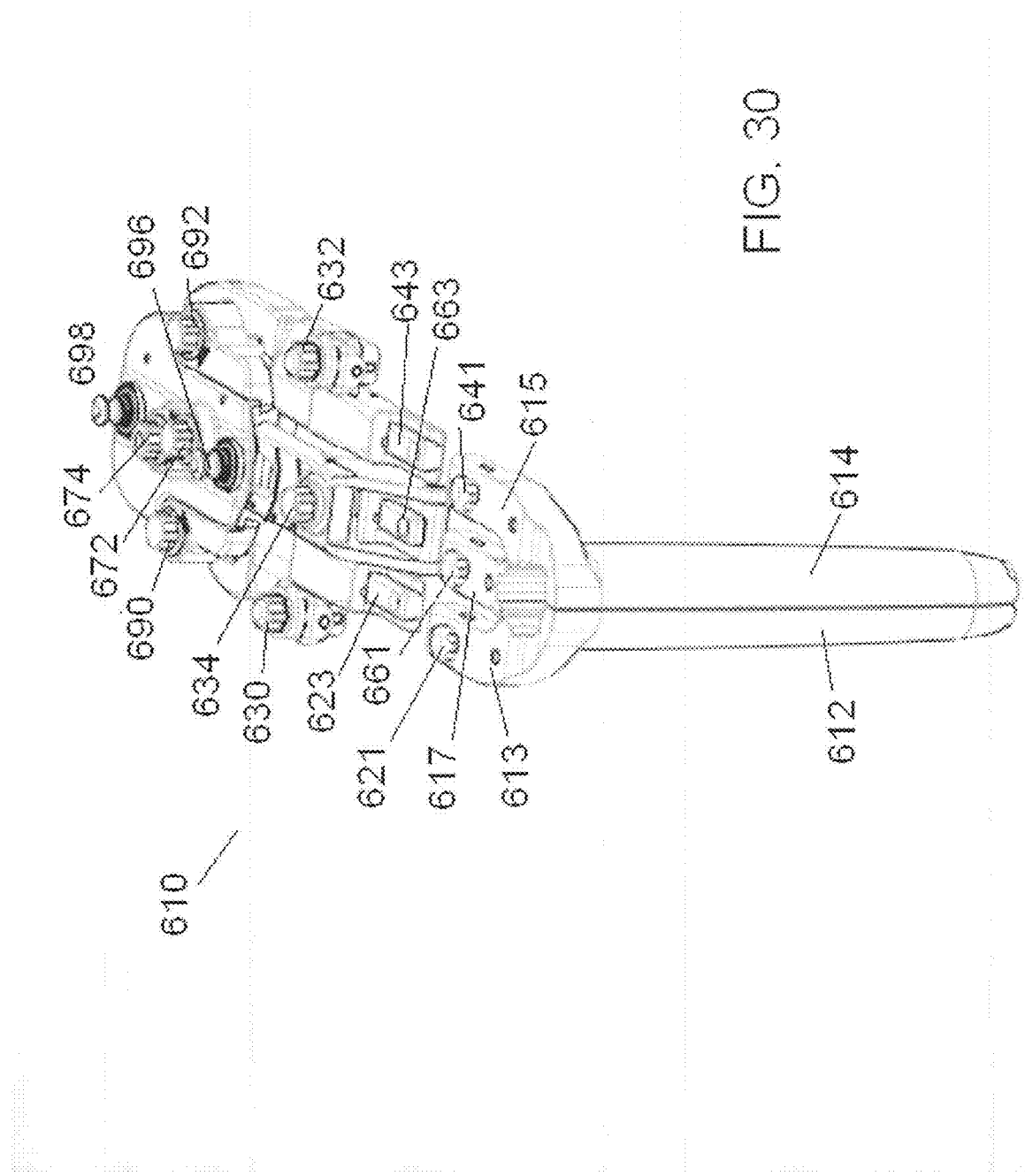
FIG. 30 depicts a top perspective view of the retractor system of FIG. 23 with its components separated from one another in accordance with some embodiments.
Figure 31:
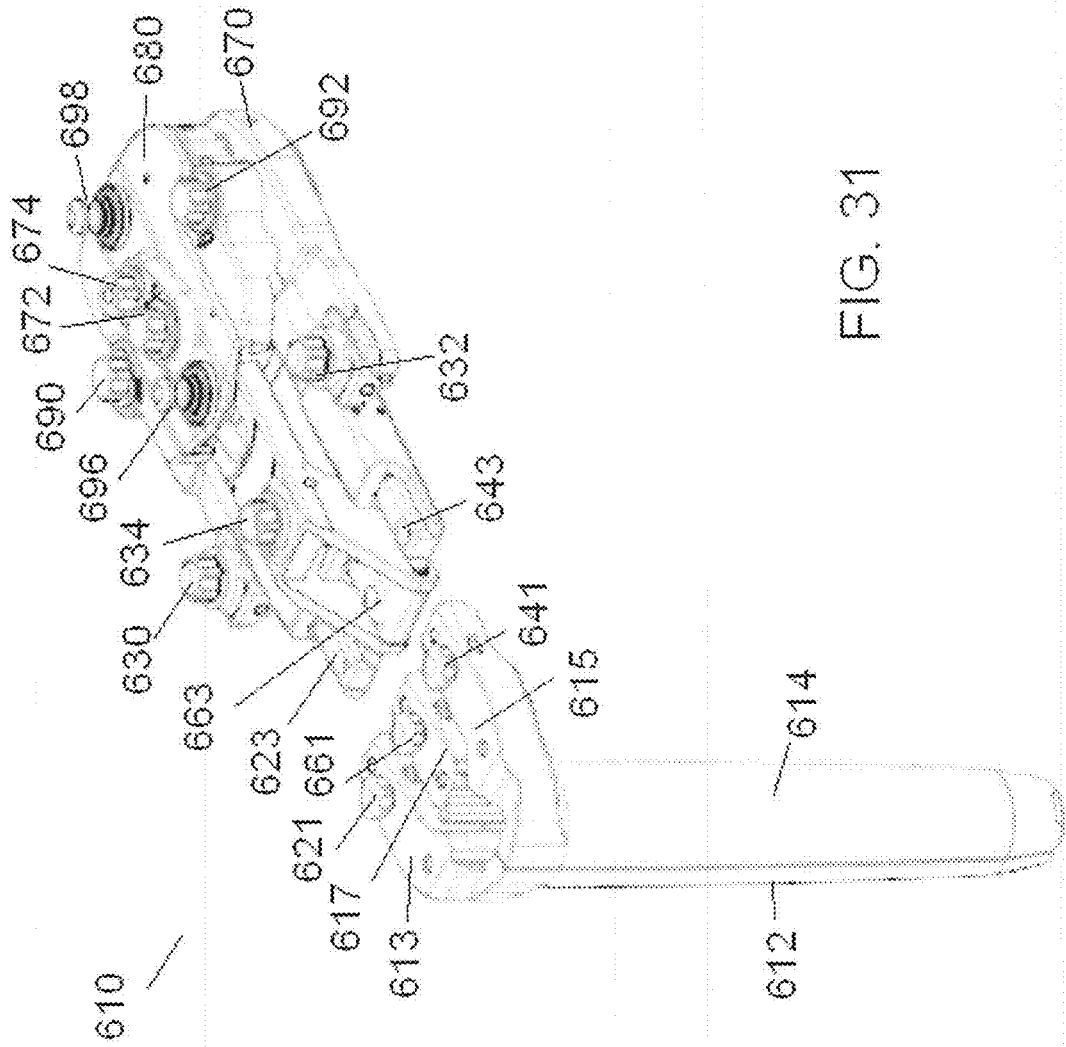
FIG. 31 depicts a different top perspective view of the retractor system of FIG. 23 with its components separated from one another in accordance with some embodiments.

FIGS. 30 and 31 depict different top perspective views of the retractor system of FIG. 23 with its components separated from one another in accordance with some embodiments. In particular, there are two distinct portions—a blade portion and a frame portion. The blade portion includes the blades 612, 614, 616 and their respective arms 613, 615, 617, while the frame portion includes the fixed plate 680, carriage 670 and all actuator knobs. From these views, one can see how the blade portion is attached to the frame portion via first, second and third fasteners 621, 641, 661 that are received through corresponding openings 623, 643, 663 formed in the frame portion.

Figure 48:
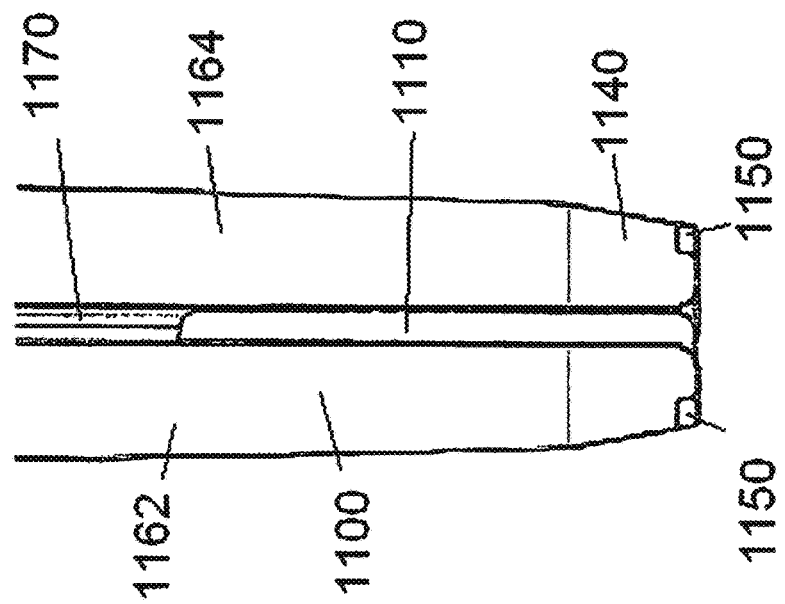
FIG. 48 depicts a side view of a portion of a retractor system including a blade having a widening shim in accordance with some embodiments.
Figure 47:
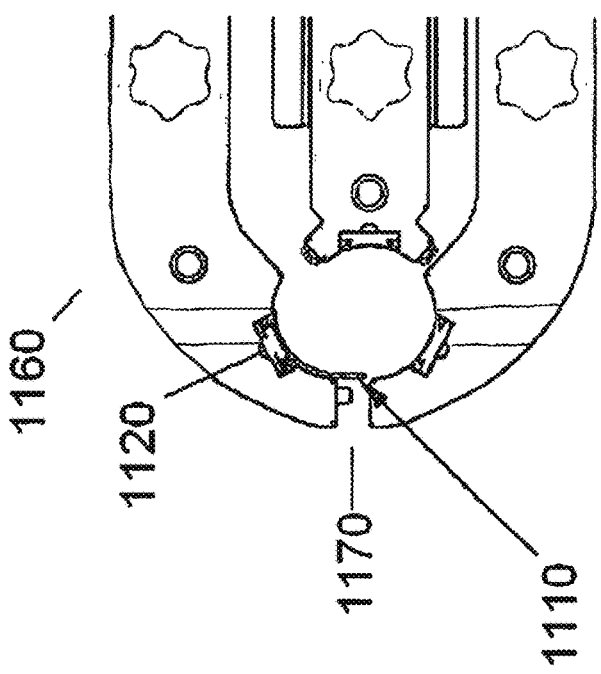
FIG. 47 depicts a top view of a portion of a retractor system including a blade having a widening shim in accordance with some embodiments.

Below are additional advantageous features that can be used with any of the retractor systems discussed above. FIGS. 32-37 illustrate blade engagement mechanisms that allow one or more blades to interlock, engage or attach to another. These engagement mechanisms, which can be in the form of one or more mating tabs, advantageously help to reduce movement between the blades, particularly when they are in a closed configuration. FIGS. 38-41 illustrate retractor blades including one or more inner sleeves for receiving a docking element, such as a docking pin. The docking pin can advantageously help to secure the blade to a vertebra, thereby helping to stabilize the blade during surgery. FIGS. 42-46 show a slidable lengthening shim that can be slid down a blade, thereby extending the tip of the blade. The lengthening shim advantageously serves to increase the tip of the blade to prevent tissue creep from occurring. FIGS. 47 and 48 show a slidable widening shim that can be slid down a blade, thereby extending the width of the blade. The widening shim advantageously serves to increase the width of the blade to prevent tissue creep from occurring. FIGS. 49-51 show a slidable disc shim that can be slid down a blade. The disc shim advantageously allows a blade to anchor into a disc space, thereby providing greater stabilization for the retractor systems and reducing the likelihood of the retractor system moving from a target site. These features are discussed in more detail below.

FIGS. 32-37 illustrate blade engagement mechanisms that allow one or more blades to interlock, engage or attach to another. FIG. 32 illustrates a top view of a portion of a retractor system 700 that can be used to retract a patient's body tissue in a surgical procedure in accordance with one embodiment of the present disclosure. From this view, one can see blade arms that attach to respective arms of a frame, such as first blade arm 710, second blade arm 720 and a third blade arm 730. The first blade arm 710 can attach to a first arm of the frame via first fastener 721. The second blade arm 720 can attach to a second arm of the frame via second fastener 741. The third blade arm 730 can attach to a third arm of the frame via third fastener 761.

In some embodiments, the first blade arm 710 can have a first blade 712 disposed within the first blade arm 710, the second blade arm 720 can have a second blade 722 disposed within the second arm 720, and the third blade arm 730 can have a third blade 732 disposed within the third blade arm 730. In some embodiments, the first and second blades 712, 722 can be deemed cranial/caudal blades, while the third blade 732 can be deemed a posterior blade, although other orientations and uses are contemplated. In some embodiments, each blade may be translated or indexed freely without a requirement to index another blade. In an embodiment shown, blade arms 710 and 720 are laterally located, and blade arm 730 is centrally located relative to the other blades arms, although other relative dispositions are contemplated within the present disclosure.

In some embodiments, the retractor system 700 can be configured to be adjusted into a desired position, and then releasably fixed to an operating table or other object in an operating room. Fixation of one or more portions of a retractor system 700 can be accomplished using, for example, one or more of an operating room table clamp, a retractor table arm, an arm clamp, a frame clamp or other similar device. Blade arms 710, 720 and 730 can each be linearly translatable to be moveable with respect to each other. In some embodiments, blade arms 710 and 720 can be mirror images of each other, although this is not required.

In some embodiments, one or more blades 712 and 722 can have an engagement mechanism 750 to engage one blade with another during installation of the retractor system or during a procedure. In some embodiments, at least one blade comprises a mateable tab, prong or extension that fits into an opening, recess or slot in another blade, thereby interlocking the blades. For example, blade 712 can have a tab 752 that can extend along a length of the blade 712, and blade 722 can have a slot 754 that can receive the tab 752 at a corresponding length of the blade 722. In some embodiments, the tab 752 can be integral to the blade 712 or a separate component. For example, in some embodiments, the tab 752 can be formed monolithically with the blade 712, or can be welded to the blade 712. In some embodiments, the slot 754 can be configured to frictionally engage with the tab 752 so that the tab 752 is fittingly received by the slot 754. The engagement mechanism 750 can stabilize the retractor system 700 by keeping the blade 712 engaged with the blade 722, and can result in stability between the arm 710 and arm 720 such as during installation of the retractor system 700 or during a procedure.

Various engagement mechanisms are contemplated by the present disclosure and are not limited to the tab 752 and slot 754 mechanisms described herein. The engagement mechanism 750 can engage, mate or lock one blade with the other, preventing movement of one blade with respect to the other during, for example, a procedure or installation of the retractor. In some exemplary embodiments, other engagement mechanisms can be used, such as a slot and a pin, a screw in a threaded hole, magnets, or other mechanisms allowing the blade 712 to be engaged or secured to the blade 722. The engagement mechanism can be integral with the blades or a separate component.

Figure 34:
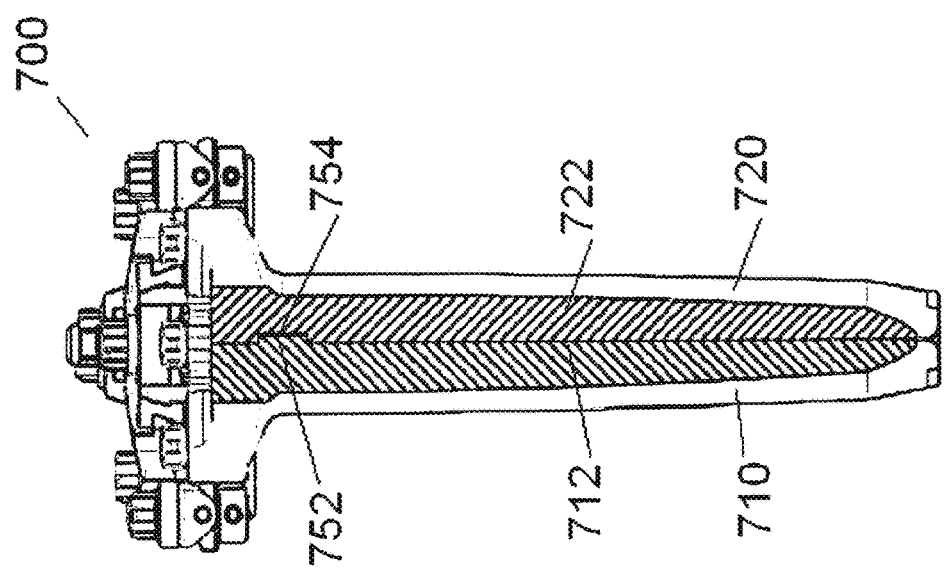
FIG. 34 depicts a front view of a portion of a three-blade retractor system in a closed or a non-retracted position in accordance with some embodiments.

FIGS. 32-34 illustrate retractor system 700 in a "closed" or non-retracted configuration, in accordance with an embodiment of the present disclosure. In the closed configuration, first blade 712, second blade 722 and third blade 732 are radially disposed around a central bore 740 to form a substantially closed, tube-shaped structure. The blades can each be independently pitched or translated, and can be independently pitched or translated with respect to other blades.

Figure 37:
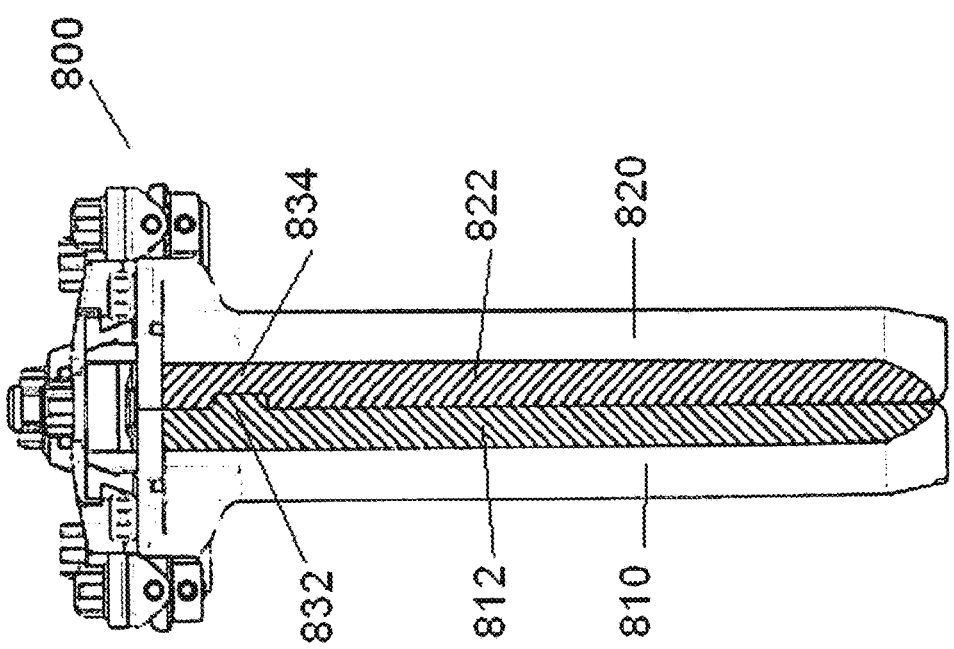
FIG. 37 depicts a front view of a portion of a two-blade retractor system in a closed or a non-retracted position in accordance with some embodiments.

In some exemplary embodiments, as shown in FIGS. 35-37, a retractor system 800 can be provided with a two-blade configuration. The retractor system 800 can comprise a first blade 812 that extends from a first blade arm 810 and a second blade 822 that extends from a second blade arm 820. In some embodiments, blades 812 and 822 can have an engagement mechanism 830 to prevent movement of one blade with respect to the other during installation of the retractor or during a procedure. For example, blade 812 can have a tab 832 that can extend along a length of the blade 812, and blade 822 can have a slot 834 that can receive the tab 832 at a corresponding length of the blade 822. In some embodiments, the slot 834 can be configured to frictionally engage with the tab 832 so that the tab 832 is fittingly received by the slot 834.

FIGS. 38-41 illustrate retractor blades including one or more inner sleeves for receiving a docking element, such as a docking pin. In some embodiments, a retractor system 900 comprises one or more blades 910 including a docking pin sleeve 920 provided therein. The docking pin sleeve 920 can be provided in an interior wall of the associated blade 910. In some embodiments, the docking pin sleeve 910 can be received within a slot 930 formed along an inner wall of the blade 910. In some embodiments, the slot 930 can allow for various instruments to slide down the blade 310 if desired. In some embodiments, a docking pin is received along the slot 930 and into the docking pin sleeve 920. The docking pin can advantageously engage bone, thereby helping to stabilize the associated retractor blade in preparation for or during a surgical procedure.

Figure 40:
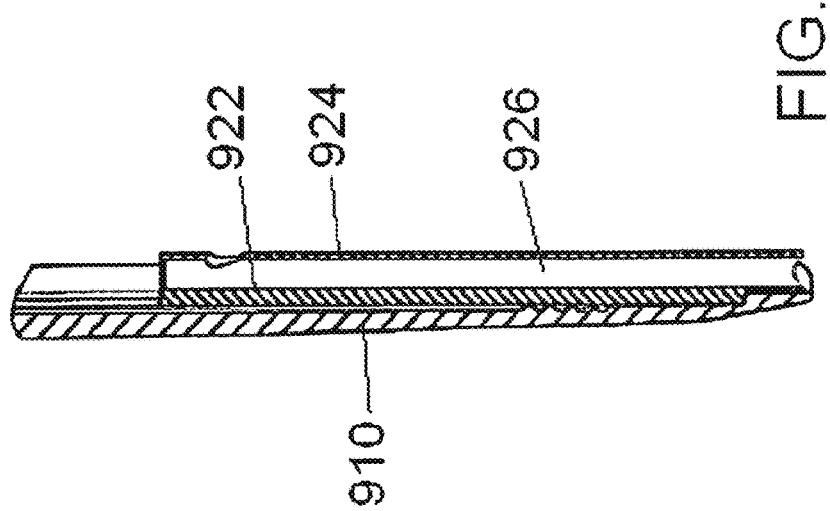
FIG. 40 depicts a cross-sectional view taken along line B-B of FIG. 38.
Figure 39:
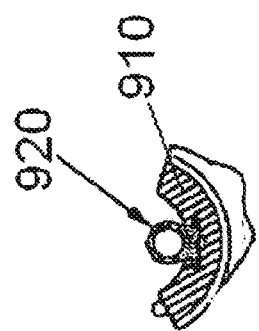
FIG. 39 depicts a cross-sectional view taken along line A-A of FIG. 38.

As shown in FIG. 39, which is a cross-sectional view of the line A-A shown in FIG. 38, in some embodiments, the docking pin sleeve 920 can be a hollow shaft within the blade 910 that allows for placement of a docking pin. In some embodiments, the docking pin sleeve 920 is a hollow cylindrical body, while in other embodiments, it can be other shapes, such as square or rectangular. As shown in FIG. 40, which is a cross-sectional view of the line B-B shown in FIG. 38, in some embodiments, one or more holes 926 are provided within the walls 922, 924 of the docking pin sleeve 920 to accommodate a docking pin.

FIG. 41 depicts a docking pin inside a docking pin sleeve in accordance with some embodiments. The docking pin 950, which can comprise a head portion and a threaded shaft, can be inserted through the docking pin sleeve 920. The docking pin 950 can slide down the docking pin sleeve 920 and can be threaded into the vertebral body to anchor the retractor blade to a bone.

FIGS. 42-46 show a slidable lengthening shim that can be slid down a blade, thereby extending the tip of the blade. The lengthening shim advantageously serves to increase the tip of the blade to prevent tissue creep from occurring. In some exemplary embodiments, as shown in FIGS. 42-46, a lengthening shim can be provided within a blade. For example, a blade 1010 can extend from a blade arm 1000, which will be attached to a retractor system frame.

A slot 1020 can be provided within the blade 1010 for instruments to slide down the slot for use in various procedures during and after installation of the retractor system. In some embodiments, a lengthening shim 1030 can be provided within the blade 1010. A lengthening shim detent tab 1040 (shown in FIG. 44) can be provided on the lengthening shim 1030 to adjust the height of the lengthening shim 1030 that extends out of the retractor arm 1000. In some exemplary embodiments, one or more detent stops 1050 (shown in FIG. 44) can be provided within the blade 1010 to engage with the lengthening shim detent tab 1040 to adjust the height of the lengthening shim 1030. Any number of detent stops 1050 can be provided at any fixed, incremental locations, and the present disclosure is not limited to any particular number or distance between the detent stops 1050. For example, in some exemplary embodiments, four detent stops 1050 can be provided in 2.5 millimeter increments where the top detent stop 1050 will keep the lengthening shim 1030 and blade 1010 flush with the bottom of the retractor arm, and the bottom detent stop 1050 will allow the lengthening shim 1030 and blade 1010 to extend below the retractor arm 1000 a distance of ten millimeters. In other words, the lengthening shim 1030 can be moved incrementally (e.g., in millimeters), with the distance traveled between the stops serving as the distance the lengthening shim 1030 can travel down the blade. The lengthening shim 1030 can advantageously incrementally increase the tip of the blade 1040 and can prevent tissue creep underneath the blade 1010. A lengthening shim removal hole 1060 can be provided to disengage the lengthening shim detent tab 1040 with the detent stop 1050, using a removal tool.

FIGS. 47 and 48 show a slidable widening shim that can be slid down a blade, thereby extending the width of the blade. The widening shim advantageously serves to increase the width of the blade to prevent tissue creep from occurring. In some exemplary embodiments, as shown in FIGS. 47 and 48, a widening shim can be provided within a blade. For example, a widening shim 1110 can be delivered down one or more blades. The widening shim prevents tissue from creeping in between adjacent blades, particularly when they are in an open configuration. The widening shim 1110 can be slidably provided down a slot 1120 formed within the blade 1100. The widening shim can be any length, and in some embodiments, is between 1-2 inches. In some exemplary embodiments, one or more detent stops can be provided along a width of the blade 1100 to engage with one or more widening shim detent tabs to adjust the widening shim 1110. Any number of detent stops can be provided at any fixed, incremental locations, and the present disclosure is not limited to any particular number or distance between the detent stops. For example, in some exemplary embodiments, ten detent stops can be provided in 1 millimeter increments to allow the widening shim 1110 to extend past the blade edge a total of ten millimeters. In some embodiments, the widening shim 1110 can advantageously prevent and block tissue creep underneath around the sides of the blade 1100. A widening shim removal hole can be provided to disengage the widening shim detent tab with the detent stop, using a removal tool.

As shown in FIG. 47, once a retractor 1160 is installed, the blades 1162, 1164 can be moved from a closed to an open (or retracted) position. A gap 1170 can exist between adjacent blades 1162, 1164. A widening shim 1110 can be slid down a blade 1162. The widening shim 1110 includes a wall that extends in between the gap 1170, thereby preventing creep from occurring in the gap 1170. In some embodiments, a widening shim can also be provided within the blade 1164 to extend towards the blade in arm 1162. For example, when the retractor is opened a distance greater than the widening shim 1110 can extend in blade 1162, a second widening shim in blade 1164 can be provided to extend past the blade 1162 toward the blade 1162. In some exemplary embodiments, etched areas 1150 can be provided along the blade tip 1140 for neuromonitoring.

FIGS. 49-51 show a slidable disc shim that can be slid down a blade. In some embodiments, a disc shim can be provided to aid a posterior blade of a retractor to be anchored into a disc space. This can provide further stabilization of the retractor and a reduced chance of the retractor moving from an initial target. Referring to FIGS. 49-51, for example, a disc shim 1210 can have an upper portion 1225 and a lower narrower portion 1215. The lower narrower portion 1215 can be inserted within a slot 1230 in the posterior blade 1220, and the upper portion can wrap around the edges of the posterior blade 1220 to keep it in place. As shown in FIG. 51, as the disc shim 1210 slides down the posterior blade 1220, into the disc, locking tabs 1260 can be provided on outer edges of the posterior blade 1220 to engage the upper portion 1225 of the disc shim 1210 and lock the disc shim 1210 in place once the disc shim 1210 is fully extended, and can prevent the disc shim 1210 from moving upwards. Further, stops 1270 can be provided along the outer edges of the posterior blade which can engage the upper portion 1225 of the disc shim 1210, and can prevent the disc shim 1210 from advancing downward too far beyond the tip 1235 of the blade 1220 distally. The lower narrower portion 1215 can allow for the posterior blade 1220 to be anchored into the disc space. In some exemplary embodiments, the disc shim 1210 can have slots which can allow the edges of the disc shim 1210 to be displaced outwards by using a removal tool. The removal tool can be threaded into the disc shim 1210 to disengage the locking tabs 1260 allowing the disc shim 1210 to be easily removed.

Figure 52:
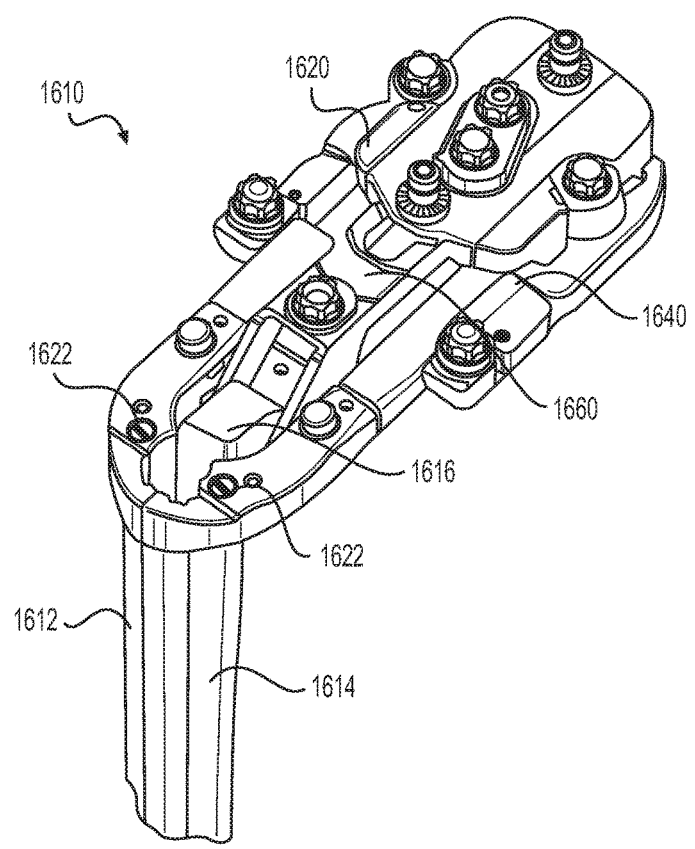
FIG. 52 depicts an alternative retractor system in a closed configuration in accordance with some embodiments.

FIGS. 52-54 depict different views of an alternative retractor system in accordance with some embodiments. The retractor system 1610 includes a number of features as in prior embodiments, including first, second, and third blades 1612, 1614, 1616; first, second, and third arms 1620, 1640, 1660; and various engagement mechanisms for independently translating and rotating the various blades and arms. The retractor system 1610 includes a frame body with a number of different actuators, which has substantially the same functionality as described for system 610 discussed above and therefore will not be repeated.

FIGS. 53A-53D show several alternative views of retractor blade 1612; although it will be appreciated that the same retractor blade features may be provided on retractor blade 1614, vice versa, or the like. Retractor blade 1612 may include one or more inner sleeves 1622 for receiving a docking element, such as a docking pin or bone pin 1650. The sleeve 1622 can be a hollow shaft or channel within or through the blade 1612 that allows for placement of a docking pin, bone pin, or the like. In some embodiments, the sleeve 1622 is a hollow cylindrical opening, while in other embodiments, it can be other shapes, such as square or rectangular. The sleeve 1622 may extend from a first end to a second end of the associated blade 1612, for example, from the proximal to distal-most end. In some embodiments, the docking pin sleeve 1622 can be received within a protrusion 1613 formed along an outer wall of the blade 1612 as best seen in FIGS. 53A and 53B. As seen in FIG. 53C, a proximal portion of the sleeve 1622 can be threaded, for example, to engage with a threaded portion of the docking pin 1650. Alternatively, the sleeve 1622 can be non-threaded or the sleeve 1622 may have threaded and non-threaded portions along its length.

The docking pin 1650 may comprise a head portion 1652 and a threaded shaft with a distal most tip 1654 that can be inserted through the docking pin sleeve 1622. The docking pin 1650 can slide down through the docking pin sleeve 1622 and can be threaded into the vertebral body to anchor the retractor blade 1612 to the bone. One advantage of threading the pin 1650 into the blade 1612 is the mechanical advantage of when the pin 1650 is being driven into the bone, for example, when the bone is very dense or hard. The docking pin 1650 can advantageously engage the bone to help to stabilize the associated retractor blades in preparation for or during a surgical procedure. As best seen in FIG. 54C, the position of the pins 1650 on the outside of the blades 1612, 1614 allows for a clear working window. Unlike other designs where the pins 1650 may be inserted through a central hole blocking the surgeons viewing window, the blade design allows the surgeon more visibility in the viewing window. In addition, a light source may be inserted at the same time with the pin 1650 further enhancing visibility.

Figure 54A:
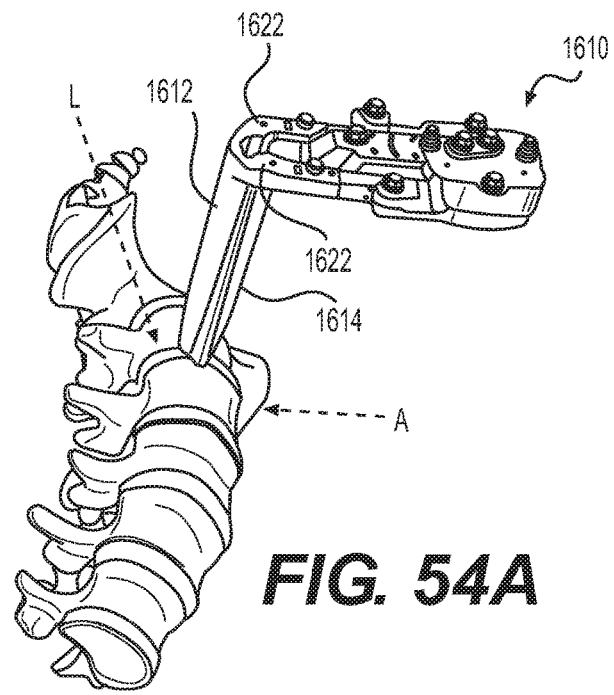
FIGS. 54A-54C show alternative views of an anterior to psoas approach to the spine using the retractor system according to one embodiment.
Figure 54B:
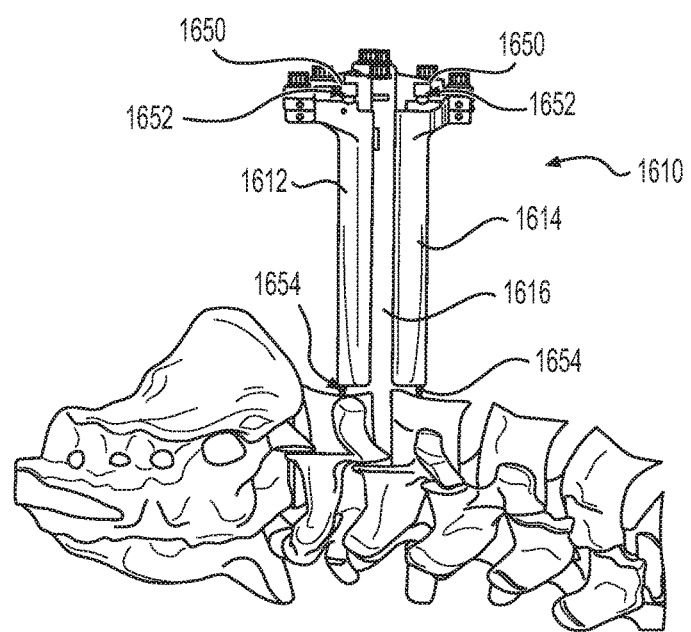
Figure 54C:
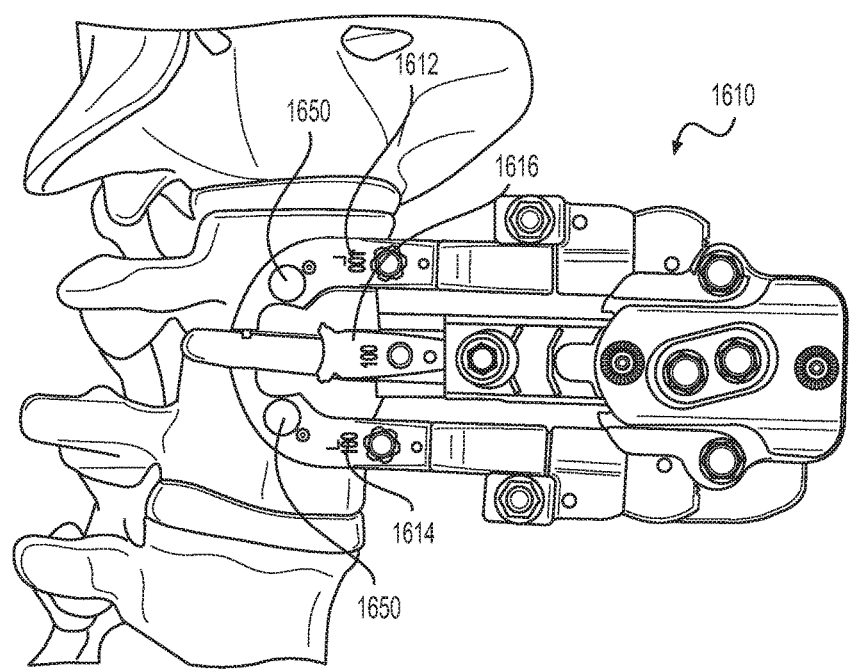

According to one method for accessing the spine depicted in FIGS. 54A-54C, an anterior to psoas approach may be advantageous. In this approach, the surgeon does not need to dissect through the psoas muscle in order to access the disc space, which typically occurs in a lateral approach, or through the abdominal cavity, which typically occurs in an anterior approach. As shown in FIG. 54A, arrow A depicts a generally anterior approach and arrow L depicts a generally lateral approach to the spine. The anterior to psoas approach, as depicted by the relative position of the retractor 1610, is angled in an orientation between the arrow A and arrow L approaches. The anterior to psoas methodology is therefore less invasive and more muscle sparing. The retractor system 1610 shown in FIG. 52 may be especially suited for this anterior t psoas approach. The orientation of the retractor 1610 during the procedure is such that the blades 1612, 1614, 1616 are angled between a direct lateral and a direct anterior with one blade (blade 1616) fully facing anterior. The retractor 1610 can be inserted in this position with all blades 1612, 1614, 1616 attached or with just the caudal and cephalad blades 1612, 1614 attached initially. If added later, the anterior blade 1616 can be inserted through the working area and swept anteriorly under the great vessels to be attached to the retractor 1610.

Figure 55A:
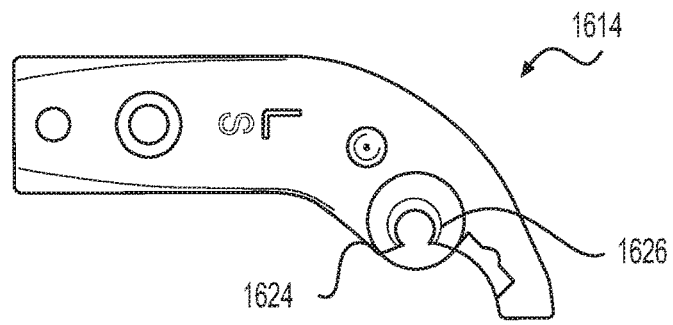
FIGS. 55A-55B show alternative views of a retractor blade with a sleeve for a bone pin according to another embodiment.
Figure 55B:
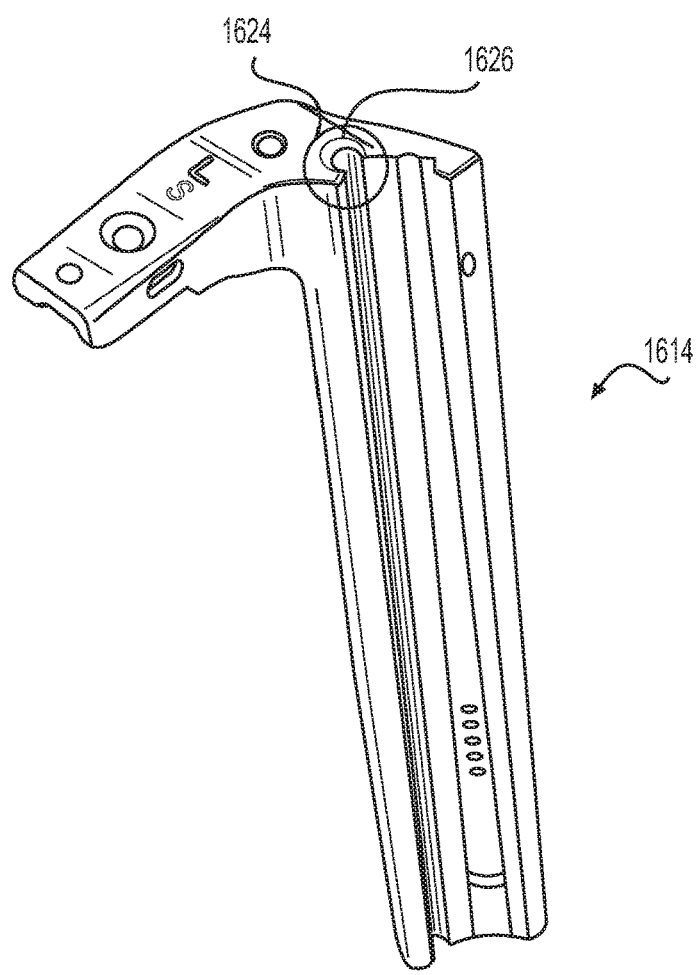

FIGS. 55A-55B show an alternative version of retractor blade 1614 where docking pin sleeve 1624 is offset through the blade 1614. The entry to the sleeve 1624 may include a chamfered or tapered surface 1626 around a portion or the entire periphery of the entry in order to enhance alignment of the pin 1650 with the sleeve. In this embodiment, the sleeve 1624 has a partially circular or semi-circular opening or channel that is in fluid communication with the interior of the blade 1614. The sleeve 1624 includes at least a partial through hole extending through the inside of the blade 1614. The sleeve 1624 is partially contained within the blade 1614, thereby moving the bone pin 1650 closer to the working channel for improved visibility while still keeping the bone pin 1650 out of the working window.

Figures 56A, 56B, 56C:
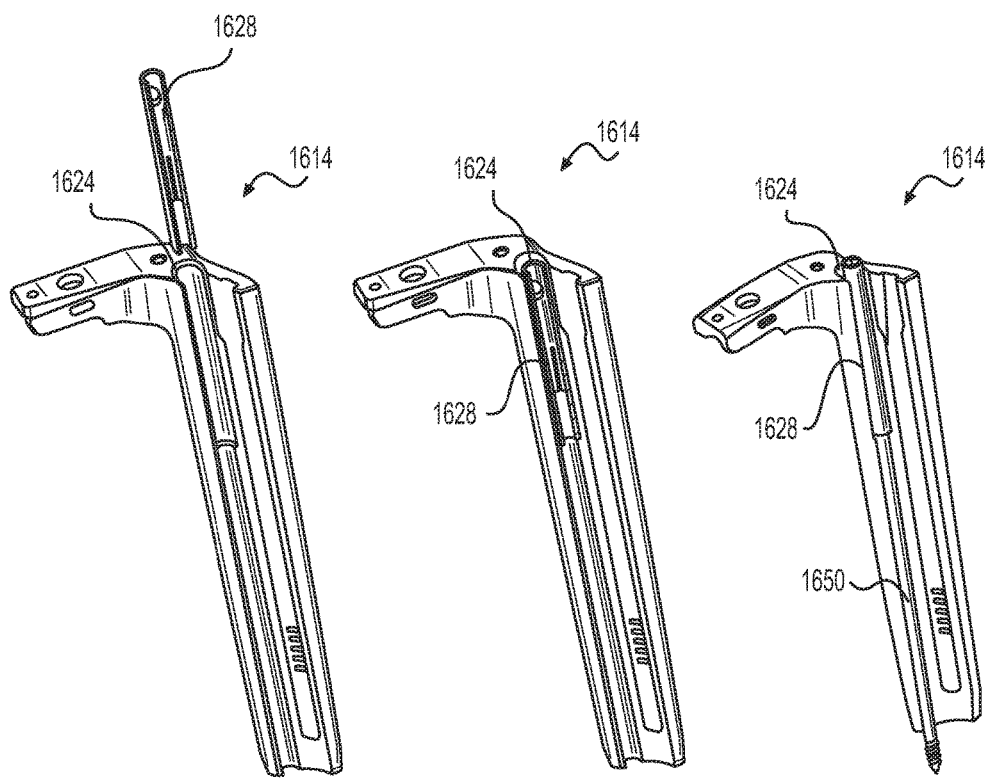
FIGS. 56A-56C depict an alternative embodiment of a retractor blade with an insert for the bone pin according to another embodiment.

FIGS. 56A-56C show another alternative embodiment for retractor blade 1614 including an insert 1628 which is at least partially received within sleeve 1624, and FIGS. 57A-57B show an embodiment of retractor blade 1614 including another version of insert 1628. Unlike a traditional sleeve or shim which may slide down inside the blade occluding the surgeon's view and working area, one or more inserts 1628 may be embedded within the blade 1614, thereby bringing the bone pin 1650 out of the working area and improving the viewing window.

The inserts 1628 may have any suitable size, shape, and configuration to mate the bone pin 1650 with the blade 1614. In one embodiment, the insert 1628 has a semi-circular cross-section shape, for example, having an outer surface designed to mate with the channel or sleeve 1624 in the retractor blade 1614 and an inner surface designed to mate with and receive at least a portion of the bone pin 1650. The insert 1628 may also include one or more openings, protrusions, or mating features, for example, on the inner or outer surfaces, configured to connect the insert 1628 to the blade and/or to the pin 1650.

The insert 1628 can vary in length, to allow more engagement on the proximal and/or distal ends of the retractor blade 1614 as needed. In FIGS. 56A-56C, the insert 1628 engages the proximal end of the retractor blade 1614 and is recessed within a portion of the sleeve 1624 of the blade 1614. As shown, the insert 1628 extends less than halfway along the length of the sleeve 1624. For example, the insert 1628 may extend about one third of the length of the blade 1614. In FIGS. 57A-57B, the insert 1628 is position along the entire length of the sleeve 1624, and therefore engages the proximal and distal ends of the blade 1614. The insert 1628 also engages a middle portion of the pin 1650, having a reduced diameter as compared to enlarged portions on the proximal and distal ends of the pin 1650. The enlarged proximal and distal ends of the pin 1650 may extend beyond the blade 1614. The insert 1628 can be separate from the bone pin 1650 or may be permanently affixed to the bone pin 1650. The insert 1628 may have substantially the same diameter as the bone pin 1650 to increase the cross sectional area of the retractor blade 1614. A portion of the insert 1628 may extend past the proximal end of the blade 1614 such that the insert 1628 and/or the pin 1650 may be inserted and/or retrieved, for example, with a tool.

Various configurations of the retractor, blades, shims, inserts, and bone pins are contemplated and are not limited by the embodiments described with reference to the figures. For example, various sizes, shapes and types of retractors, blades, shims, inserts, and bone pins are contemplated, and various materials can be used to construct the various parts. For example, the retractor and its constituent components may be fabricated from any one or more, or combinations of, metals, polymers, carbon fiber or other composites, natural materials or any other materials having sufficient strength, durability and biocompatibility. Material selected can be radiolucent or radiopaque, as desired. The exemplary embodiments of the present disclosure provide various advantages, such as providing stability of the blades of the retractor, securing the retractor and preventing tissue creep.

All references cited herein are expressly incorporated by reference in their entirety. It will be appreciated by persons skilled in the art that the present invention is not limited to what has been particularly shown and described herein above. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A surgical retractor system comprising:
    a frame portion having a first blade arm defining proximal and distal ends and a first arm longitudinal axis extending therebetween, a second blade arm defining proximal and distal ends and a second arm longitudinal axis extending therebetween, and a third blade arm defining proximal and distal ends and a third arm longitudinal axis extending therebetween;
    a first blade having an inner wall, an opposite outer wall and a protrusion formed along the outer wall of the first blade, the first blade operably attached to the distal end of the first blade arm, wherein the protrusion extends continuously along a length of the outer wall of the first blade;
    a second blade operably attached to the distal end of the second blade arm; and
    a third blade operably attached to the distal end of the third blade arm;
    a bone pin having a head portion and a distal tip portion,
    wherein the first and second blades are configured to move in a cephalad-caudal direction and the third blade is configured to move in an anterior-posterior direction, and the first blade comprises an opening along the inner wall extending from a first end of the first blade, proximate to the first blade arm, to a second end of the first blade disposed on a distal portion of the first blade, the opening configured to receive the bone pin and engage adjacent bone,
    wherein the bone pin is configured such that, when inserted into the opening, the head portion is disposed proximate the first end of the first blade and the distal tip portion traverses beyond the distal portion of the first blade, and
    wherein the first arm longitudinal axis, the second arm longitudinal axis, and the third arm longitudinal axis are generally parallel.

2. The surgical retractor system of claim 1, wherein the opening is a partial channel in fluid communication with an interior of the first blade.

3. The surgical retractor system of claim 2, wherein the partial channel extends along an entire length of the first blade.

4. The surgical retractor system of claim 2, wherein the partial channel has a semi-circular cross-section.

5. The surgical retractor system of claim 2, further comprising an insert received along a length of the partial channel, the insert configured to receive a portion of the bone pin.

6. The surgical retractor system of claim 1, wherein an entry to the opening at the first end of the first blade is tapered around a periphery of the entry.

7. The surgical retractor system of claim 1, wherein a portion of the opening is threaded and engages a threaded portion on the bone pin.

8. The surgical retractor system of claim 1, wherein the second blade comprises an opening extending from a first end of the second blade to a second end of the second blade, the opening of the second blade configured to receive a second bone pin and engage a second adjacent bone.

9. The surgical retractor system of claim 1, wherein each of the first blade, second blade, and third blade can be translated and angulated independently from one another.

10. A surgical retractor system comprising:
    a frame portion having a first blade arm defining proximal and distal ends and a first arm longitudinal axis extending therebetween, a second blade arm defining proximal and distal ends and a second arm longitudinal axis extending therebetween, and a third blade arm defining proximal and distal ends and a third arm longitudinal axis extending therebetween;
    a first bone pin having a head portion and a distal most tip portion;
    a first blade having an inner wall, an opposite outer wall and a protrusion formed along the outer wall of the first blade, the first blade operably attached to the distal end of the first blade arm, the first blade comprising a first opening along the inner wall extending from a first end of the first blade, proximate to the first blade arm, to a second end of the first blade disposed on a distal portion of the first blade, the first opening configured to receive the first bone pin and engage a first adjacent bone, wherein the protrusion extends continuously along a length of the outer wall of the first blade;

a second blade operably attached to the distal end of the second blade arm, the second blade comprising a second opening extending from a first end of the second blade to a second end of the second blade, the second opening configured to receive a second bone pin and engage a second adjacent bone; and a third blade operably attached to the distal end of the third blade arm, wherein the first and second blades are configured to move in a cephalad-caudal direction and the third blade is configured to move in an anterior-posterior direction, wherein the first bone pin is configured such that, when inserted into the first opening, the head portion is disposed proximate the first end of the first blade and the distal tip portion traverses beyond the distal portion of the first blade, and wherein the first arm longitudinal axis, the second arm longitudinal axis, and the third arm longitudinal axis are generally parallel.

11. The surgical retractor system of claim 10, wherein each of the first and second openings is a partial channel in fluid communication with an interior of the first blade and second blade, respectively.

12. The surgical retractor system of claim 11, wherein the partial channels extend along an entire length of the first and second blades, respectively.

13. The surgical retractor system of claim 11, wherein the partial channels each have a semi-circular cross-section.

14. The surgical retractor system of claim 10, wherein an entry to each of the first and second openings at the first ends of the first and second blades, respectively, is tapered around a periphery of the entry.

15. The surgical retractor system of claim 10, wherein a portion of the first and second openings are threaded and engage a threaded portion on the first and second bone pins, respectively.

16. The surgical retractor system of claim 10, wherein each of the first blade, second blade, and third blade can be translated and angulated independently from one another.

* * * * *